United States Patent
Sardone et al.

(10) Patent No.: US 10,836,727 B2
(45) Date of Patent: Nov. 17, 2020

(54) CRYSTAL FORMS OF LENVATINIB

(71) Applicant: Indena S.P.A., Milan (IT)

(72) Inventors: Nicola Sardone, Milan (IT); Stefano Luca Giaffreda, Medicina (IT); Andrea Gambini, Milan (IT); Alex Petrolati, Medicina (IT); Pietro Allegrini, Milan (IT); Enrico Modena, Medicina (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 16/334,027

(22) PCT Filed: Sep. 15, 2017

(86) PCT No.: PCT/EP2017/073354
§ 371 (c)(1),
(2) Date: Mar. 18, 2019

(87) PCT Pub. No.: WO2018/054792
PCT Pub. Date: Mar. 29, 2018

(65) Prior Publication Data
US 2019/0256473 A1    Aug. 22, 2019

(30) Foreign Application Priority Data
Sep. 21, 2016   (EP) .................................... 16189825

(51) Int. Cl.
C07D 215/48    (2006.01)

(52) U.S. Cl.
CPC ........ C07D 215/48 (2013.01); C07B 2200/13 (2013.01)

(58) Field of Classification Search
CPC .................................................. C07D 215/48
USPC .......................................... 546/162; 514/312
See application file for complete search history.

(56) References Cited

U.S. PATENT DOCUMENTS 6,627,646 B2 * 9/2003 Bakale ................ C07D 401/12
514/303

FOREIGN PATENT DOCUMENTS

| EP | 1698623 A1 | 9/2006 |
| EP | 1797881 A1 | 6/2007 |
| EP | 1894918 A1 | 3/2008 |

OTHER PUBLICATIONS

Guillory (in Brittain ed.), "Polymorphism in Pharmaceutical Solids" NY:Marcel Dekker, Inc. 1-2, 183-226; 235-238. (Year: 1999).*
CMU Pharmaceutical polymorphism, Internet p. 1-3 Apr. 3, 2008. (Year: 2002).*
Singhal et al., "Drug Polymorphism, etc.," Advanced Drug Reviews 56, p. 335-347. (Year: 2004).*
Concise Encyclopedia Chemistry, NY: Walter de Gruyter, 872-873. (Year: 1993).*
Jain et al., "Polymorphism in Pharmacy", Indian Drugs, 23(6) 315-329. (Year: 1986).*
Muzaffer et al., "Polymorphism and Drug Availabity, etc.," J of Pharm. (Lahore), 1(1), 59-66. (Year: 1979).*
U.S. Pharnnacopia #23, National Formulary #18, 1843-1844. (Year: 1995).*
Doelker, english translation of S.T.P. Pratiques, 9(5), 399-409, pp. 1-33. (Year: 1999).*
Doelker, english translation of Ann. Pharm. Fr., 60: 161-176, pp. 1-39. (Year: 2002).*
Taday et al., "Using Terahertz, etc.," J of Pharm. Sci., 92(4), 831-838. (Year: 2003).*
Otuska et al., "Effect of Polymorphic, etc.," Chem. Pharm. Bull. 47(6) 852-856. (Year: 1999).*
Caira M.R., "Crystalline polymorphism of organic compounds", Topics in Current Chemistry, vol. 198, Jan. 1, 1998 pp. 163-208.
Search Report and Written Opinion of PCT/EP2017/073354 dated Jan. 9, 2018.

* cited by examiner

*Primary Examiner* — Patricia L Morris
(74) *Attorney, Agent, or Firm* — Silvia Salvadori, P.C.; Silvia Salvadori

(57) ABSTRACT

The present invention provides novel crystalline forms of 4-[3-Chloro-4-(N'-cyclopropylureido)phenoxy]-7-methoxy-quinoline-6-carboxamide methanesulfonate, as well as methods for their preparation.

1 Claim, 37 Drawing Sheets

CRYSTAL FORMS OF LENVATINIB

This application is a U.S. national stage of PCT/EP2017/073354 filed on 15 Sep. 2017, which claims priority to and the benefit of European Application No. 16189825.9 filed on 21 Sep. 2016, the contents of which are incorporated herein by reference in their entireties.)

BACKGROUND OF THE INVENTION

Lenvatinib, 4-[3-Chloro-4-(N'-cyclopropylureido)phenoxy]-7-methoxyquinoline-6-carboxamide methanesulfonate, of formula (I)

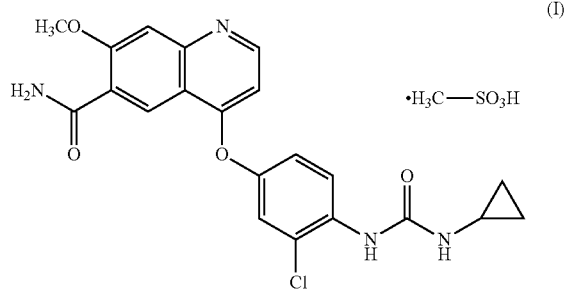

is an anti-cancer drug for the treatment of certain kinds of thyroid cancer, and potentially for other cancers as well. It acts as a multiple kinase inhibitor against the VEGFR1, VEGFR2 and VEGFR3 kinases. (Matsui, J. et al., *Clinical Cancer Research* 14 (17): 5459-65.

Lenvatinib is used for the treatment of differentiated thyroid cancer that is either locally recurrent or metastatic, progressive, and did not respond to treatment with radioactive iodine (radioiodine)—Haberfeld, H, ed. (2015). *Austria-Codex* (in German). Vienna: Österreichischer Apothekerverlag; FDA Professional Drug Information for Lenvima.

Lenvatinib is known to have a rather complex polymorphic behavior. Usually the most preferred forms employed in pharmaceutical preparations are the monohydrate or the anhydrous forms. The known crystalline forms, labeled as A, B, C, F, I and DMSO solvate, are described in US 2007/0078159. The amorphous form is described in EP 1 894 918.

There is a strong interest in making available new crystalline forms of Lenvatinib easy to obtain and having the required chemical and physical characteristics.

DESCRIPTION OF THE INVENTION

The invention concerns novel polymorphs of Lenvatinib mesylate, namely to crystal forms characterized by XPRD data and designated as DMSO-1, DMSO-2, ACA-1, ACA-1 HT dry, CHF-1, FOA-1 and $H_2O$-1

The invention is also directed to processes for the preparation of said forms comprising crystallization or re-crystallization from appropriate solvents.

The invention is further directed to pharmaceutical compositions comprising the novel Lenvatinib mesylate crystalline forms.

The new crystal forms were prepared by:
- extended stirring (slurry) at room temperature of Lenvatinib mesylate suspensions in different antisolvents or solvent/antisolvent mixtures (CHF-1 form);
- thermal treatment at high temperature of powdered solvate forms (ACA-1-HT form);
- evaporation of solution or viscous suspension in different temperature/pressure conditions (ACA-1, $H_2O$-1 forms).

The X-ray powder diffractogram (XRPD) has been obtained using the instrument X'Pert PRO PANalytical with single scan, using Kα1 radiation. The diffractogram is measured in reflection mode in the range 3-40° 2θ.

The FT-Raman spectrum (Fourier transform Raman spectroscopy) was recorded with the Nicolet iS50. The excitation source was a Nd-YAG laser (1064 nm) in the backscattering (180°) configuration. The focused laser beam diameter was approx. 50 um and the spectral resolution 4 $cm^1$. The spectra were recorded with a laser power at the sample of approx. 100 mW. DSC analyses were carried out using a differential scanning calorimeter DSC1 Mettler Toledo. The samples were heated at a heating rate of 10 K/min in the temperature range from −25 to 320° C.

The thermograms were obtained using the TGA/DSC1 Mettler Toledo thermo-balance. The samples were heated from 25° C. to 450° C. at 10 K/min.

The crystal forms of Lenvatinib mesylate of the invention have surprisingly interesting chemical-physical characteristics. They are in particular characterized by high level of chemical purity as well as by good handling characteristics for the preparation of pharmaceutical compositions.

Details of the preparation and of the characterization of the forms of the invention are reported in the following examples.

Example 1: DMSO-1 form

Lenvatinib Mesylate (10-50 mg) was dissolved/suspended in DMSO (100-200 µL), at a temperature ranging from room temperature to the boiling point of the solvent, to give a solution or suspension. The solution/suspension was left under stirring (1-16 hours) and then filtered to obtain a clear solution.

An anti-solvent (0.5-4.0 mL) was added dropwise to the DMSO solution under stirring at a temperature ranging from 20 to 40° C. The anti-solvents used were esters (preferably ethyl formate, ethyl acetate and isopropyl acetate), ethers (preferably THF and 1,2-dimethoxyethane), alcohols (preferably ethanol and 2-propanol), chlorinated solvents (preferably chloroform and dichloromethane), and polar aprotic solvents (preferably acetonitrile).

After 30-180 minutes the precipitate was recovered under vacuum.

The DMSO-1 form of the invention is a hydrate crystal form.

The solid was recovered in a yield ~96% and high level of chemical purity (>99.5%).

Figure 1:
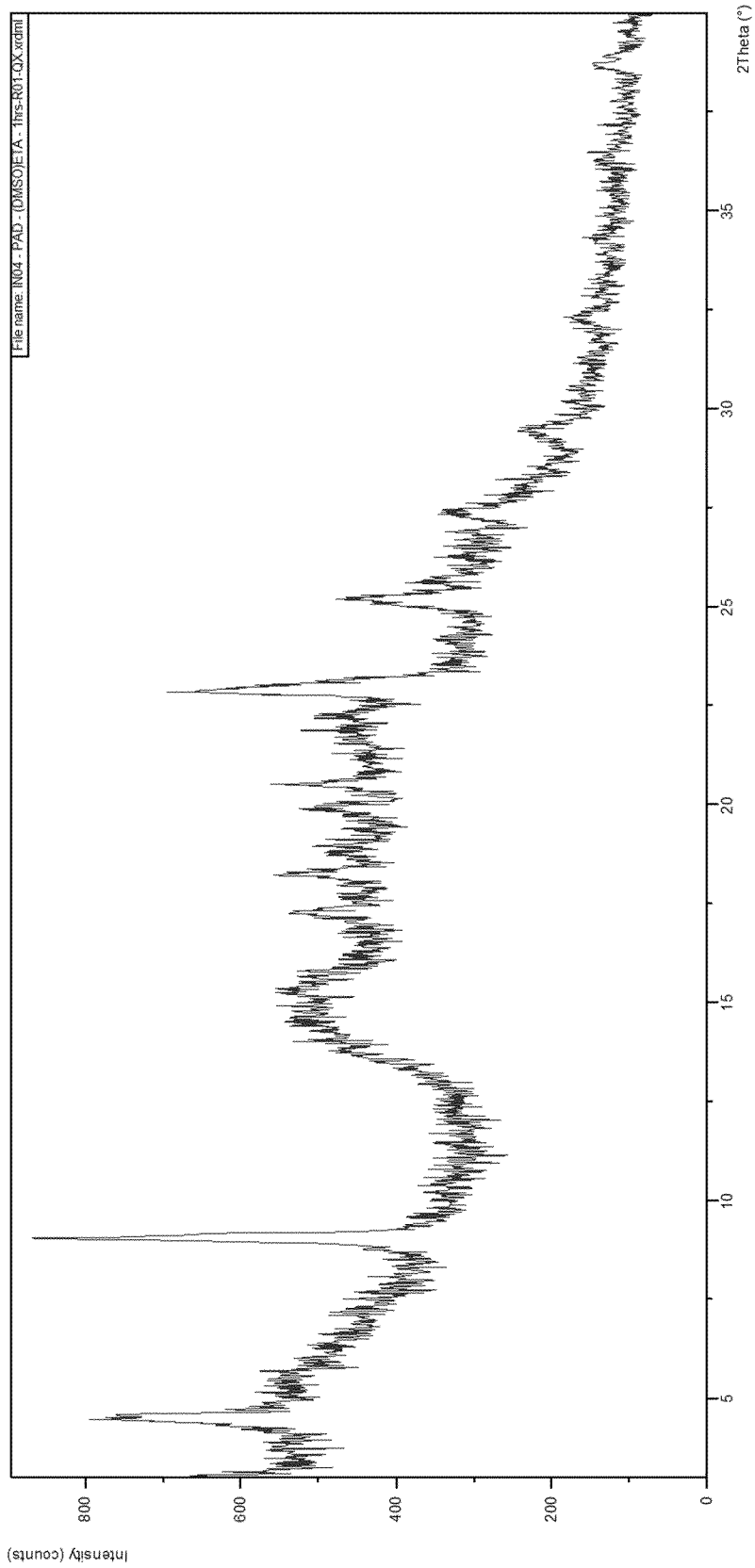
FIG. 1: XRPD spectrum of Lenvatinib, form DMSO-1

The new crystal form DMSO-1 is characterized by the XRPD spectrum shown in FIG. 1. Main peaks at 2theta±0.3 degrees are: 4.5, 9.0, 22.8, 25.2.

Table 1 below shows the significant peaks of the spectrum.

TABLE 1

| XRPD peak list | | | | |
|---|---|---|---|---|
| Pos. [°2Th.] | Height [cts] | FWHM [°2Th.] | d-spacing [Å] | Rel. Int. [%] |
| 4.5429 | 248.09 | 0.2007 | 19.45152 | 52.51 |
| 9.0235 | 472.43 | 0.0836 | 9.80039 | 100.00 |
| 15.4862 | 92.07 | 0.5353 | 5.72203 | 19.49 |
| 17.2633 | 100.86 | 0.1004 | 5.13680 | 21.35 |
| 18.2150 | 108.87 | 0.2007 | 4.87049 | 23.05 |
| 18.7118 | 35.46 | 0.4015 | 4.74229 | 7.51 |
| 19.9001 | 76.88 | 0.2676 | 4.46170 | 16.27 |
| 20.5089 | 128.13 | 0.1004 | 4.33062 | 27.12 |
| 22.8334 | 334.74 | 0.0836 | 3.89474 | 70.86 |
| 25.2097 | 155.03 | 0.1338 | 3.53275 | 32.82 |
| 27.3991 | 86.96 | 0.2676 | 3.25523 | 18.41 |
| 29.4589 | 56.68 | 0.3346 | 3.03214 | 12.00 |
| 32.2925 | 47.61 | 0.2676 | 2.77226 | 10.08 |
| 36.2486 | 25.73 | 0.3346 | 2.47826 | 5.45 |
| 38.6625 | 47.57 | 0.1338 | 2.32891 | 10.07 |

Figure 2:
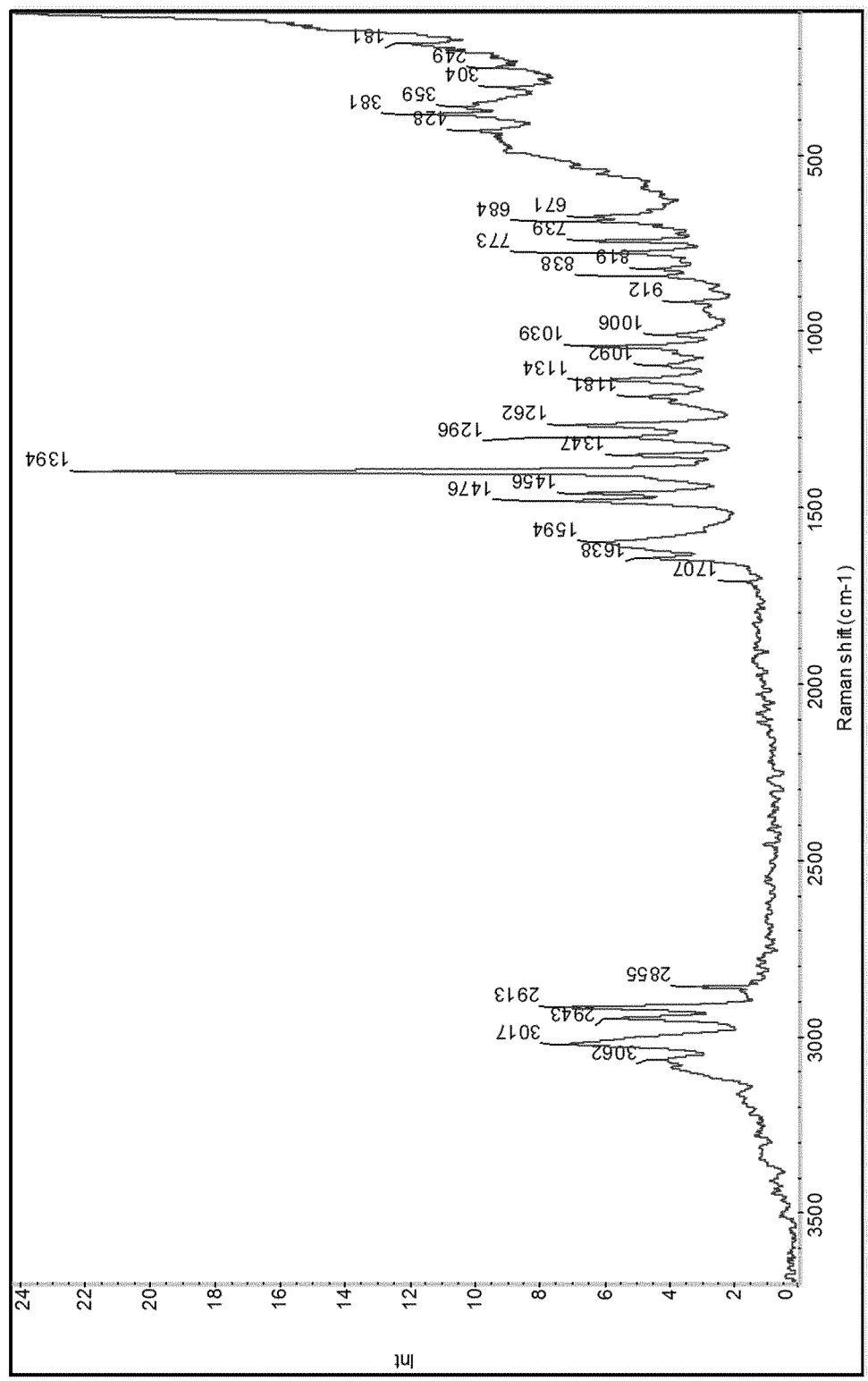
FIG. 2: FT-Raman spectrum of Lenvatinib, form DMSO-1

FT-Raman analysis returns the spectrum shown in FIG. 2 showing the characteristic bands of form DMSO-1.

Figure 3:
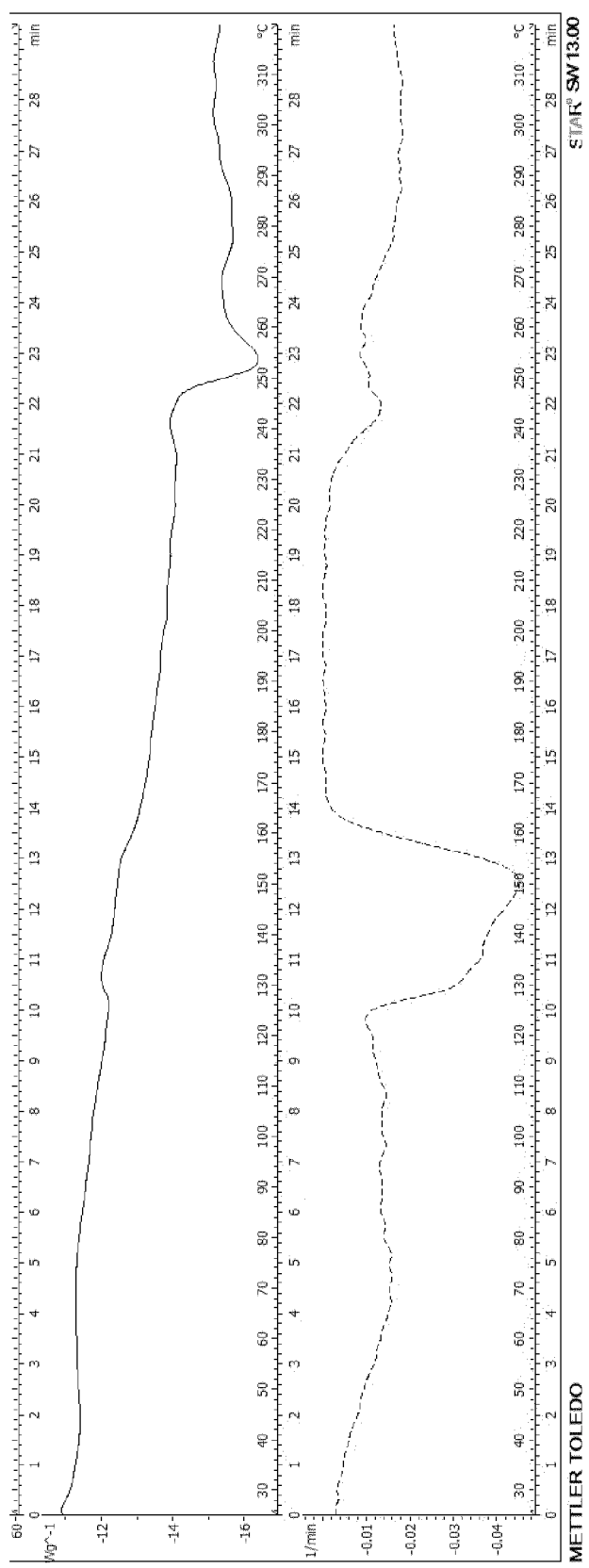
FIG. 3: DSC analysis of Lenvatinib, form DMSO-1

DSC analysis, shown in FIG. 3, does not evidence important endothermic events.

Figure 4:
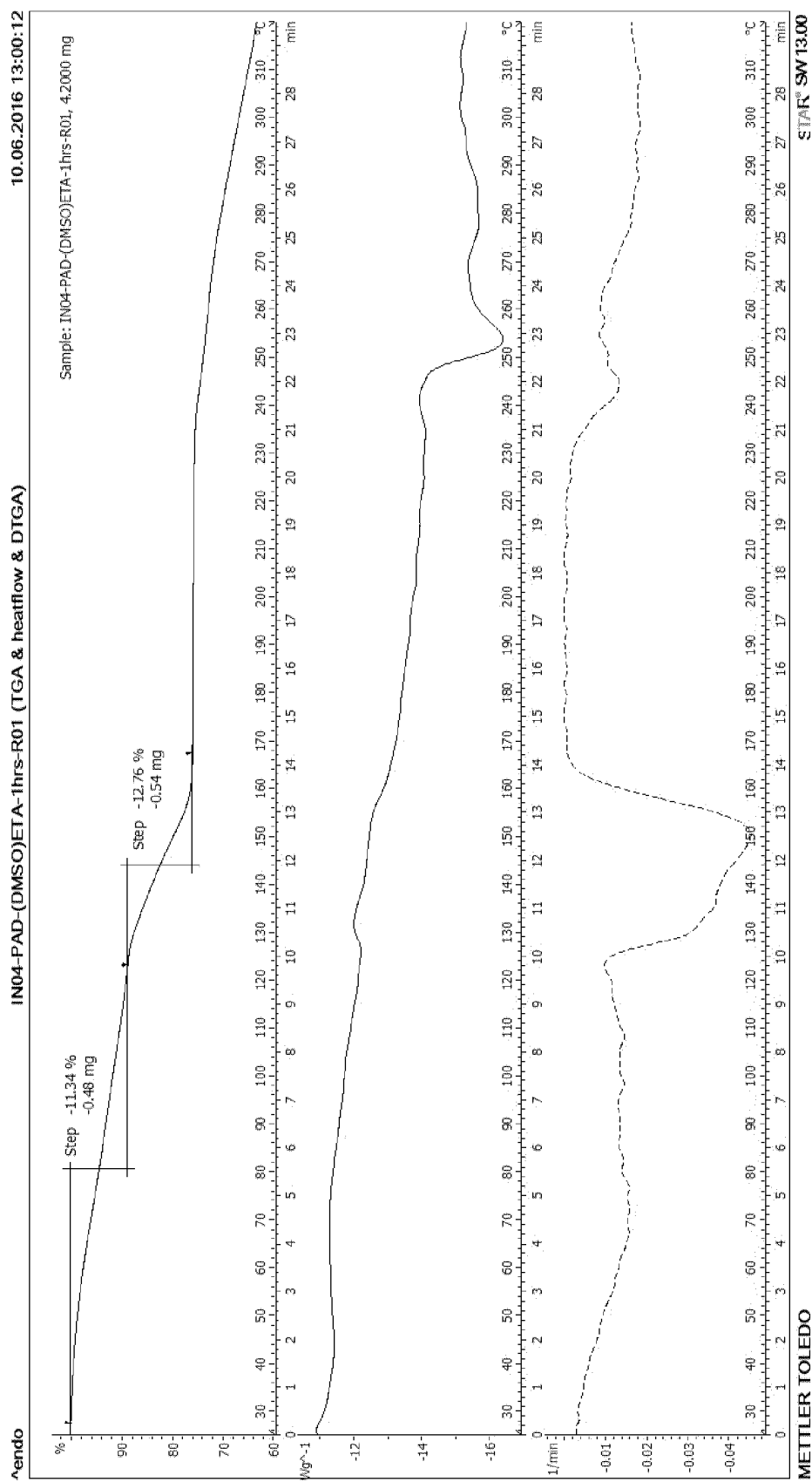
FIG. 4: TGA analysis of Lenvatinib, form DMSO-1
Figure 5:
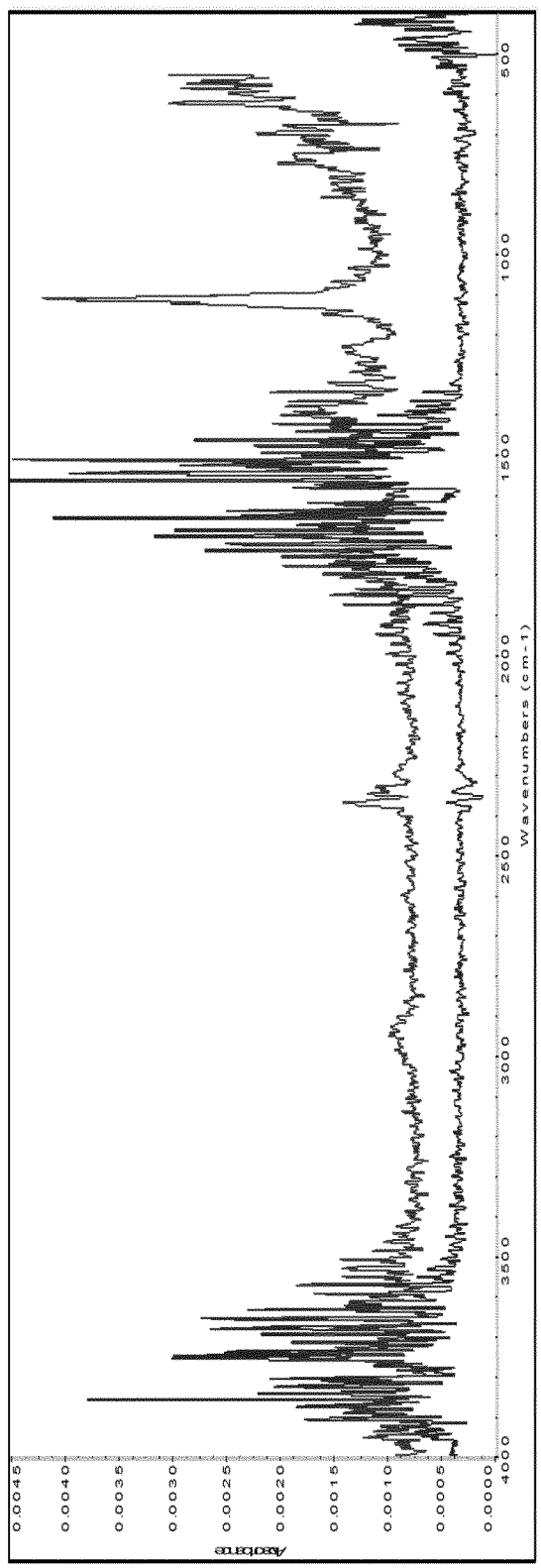
FIG. 5: EGA analysis of Lenvatinib, form DMSO-1
Figure 6:
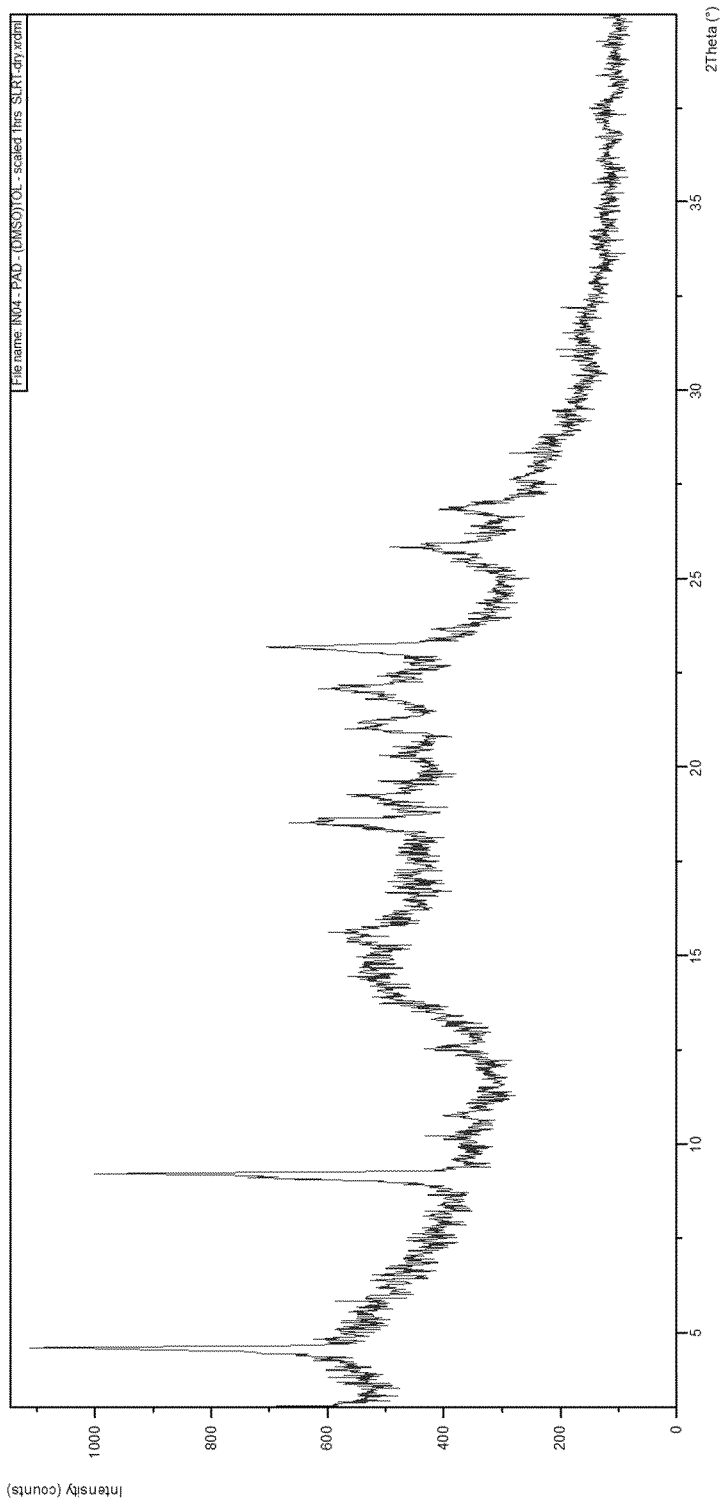
FIG. 6: XRPD spectrum of Lenvatinib, form DMSO-2

The TGA analysis, shown in FIG. 4, highlights two weight losses: the first of 11.3% and the second of 12.8%. EGA analysis, shown in FIG. 5, highlights the evolution of water. Above 220° C. the melting/degradation of the sample occur.

Example 2: DMSO-2 Form

Lenvatinib Mesylate (10-50 mg) was dissolved/suspended in DMSO (100-200 µL), at a temperature ranging from room temperature to the boiling point of the solvent, to give a solution or suspension. The solution/suspension was left under stirring (1-16 hours) and then filtered to obtain a clear solution.

An anti-solvent (0.5-4.0 mL) was added dropwise to the DMSO solution under stirring at a temperature ranging from 20 to 40° C. The anti-solvents used were aromatic hydrocarbons (preferably toluene) and apolar ethers (preferably TBME).

After 30-180 minutes the precipitate was recovered under vacuum and washed with TBME.

The Lenvatinib mesylate DMSO-2 of the invention is a hydrate crystal form.

The solid was recovered in a yield ~96% and high level of chemical purity (>99.5%)

Figure 13:
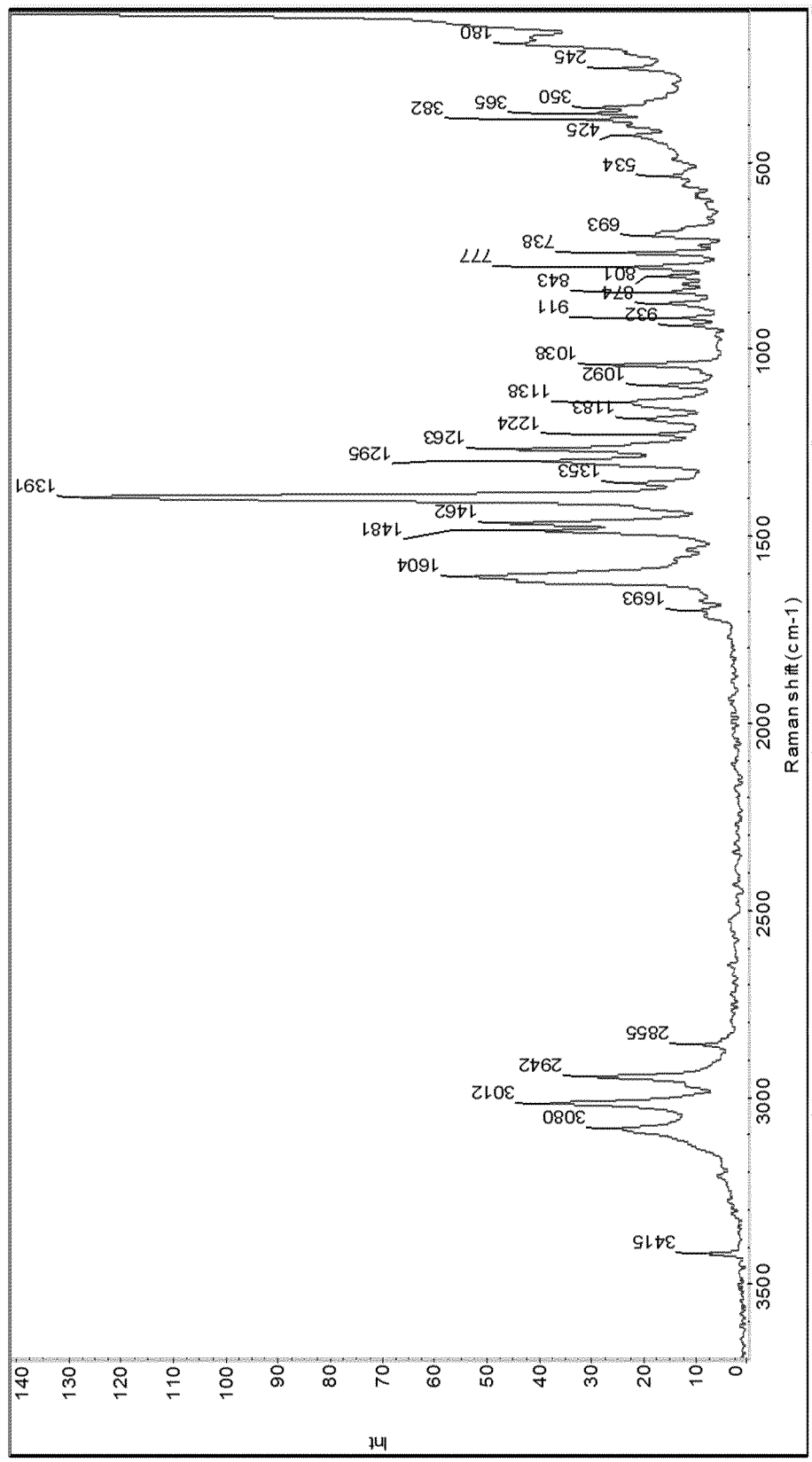
FIG. 13: FT-Raman spectrum of Lenvatinib, form ACA-1.

The new crystal form DMSO-2 is characterized by the XRPD spectrum shown in FIG. 13. Main peaks at 2theta±0.3 degrees are: 4.6, 9.2, 15.6, 18.8, 22.1, 23.2.

Table 2 below shows the significant peaks of the spectrum.

TABLE 2

| XRPD peak list | | | | |
|---|---|---|---|---|
| Pos. [°2Th.] | Height [cts] | FWHM [°2Th.] | d-spacing [Å] | Rel. Int. [%] |
| 4.5837 | 606.74 | 0.0669 | 19.27843 | 97.96 |
| 9.2097 | 619.40 | 0.0502 | 9.60272 | 100.00 |
| 12.5481 | 69.54 | 0.1004 | 7.05441 | 11.23 |
| 13.8887 | 109.17 | 0.5353 | 6.37637 | 17.63 |
| 15.6527 | 139.24 | 0.4015 | 5.66152 | 22.48 |
| 18.5731 | 161.14 | 0.1673 | 4.77739 | 26.02 |
| 19.2159 | 114.87 | 0.1338 | 4.61900 | 18.54 |
| 21.0908 | 114.94 | 0.3346 | 4.21244 | 18.56 |
| 22.1037 | 189.44 | 0.1338 | 4.02164 | 30.58 |
| 23.1879 | 336.03 | 0.0669 | 3.83600 | 54.25 |
| 25.8843 | 136.23 | 0.2007 | 3.44219 | 21.99 |
| 26.8671 | 125.45 | 0.1673 | 3.31846 | 20.25 |
| 31.7064 | 17.83 | 0.8029 | 2.82215 | 2.88 |
| 37.5436 | 24.74 | 0.6691 | 2.39570 | 3.99 |

Figure 7:
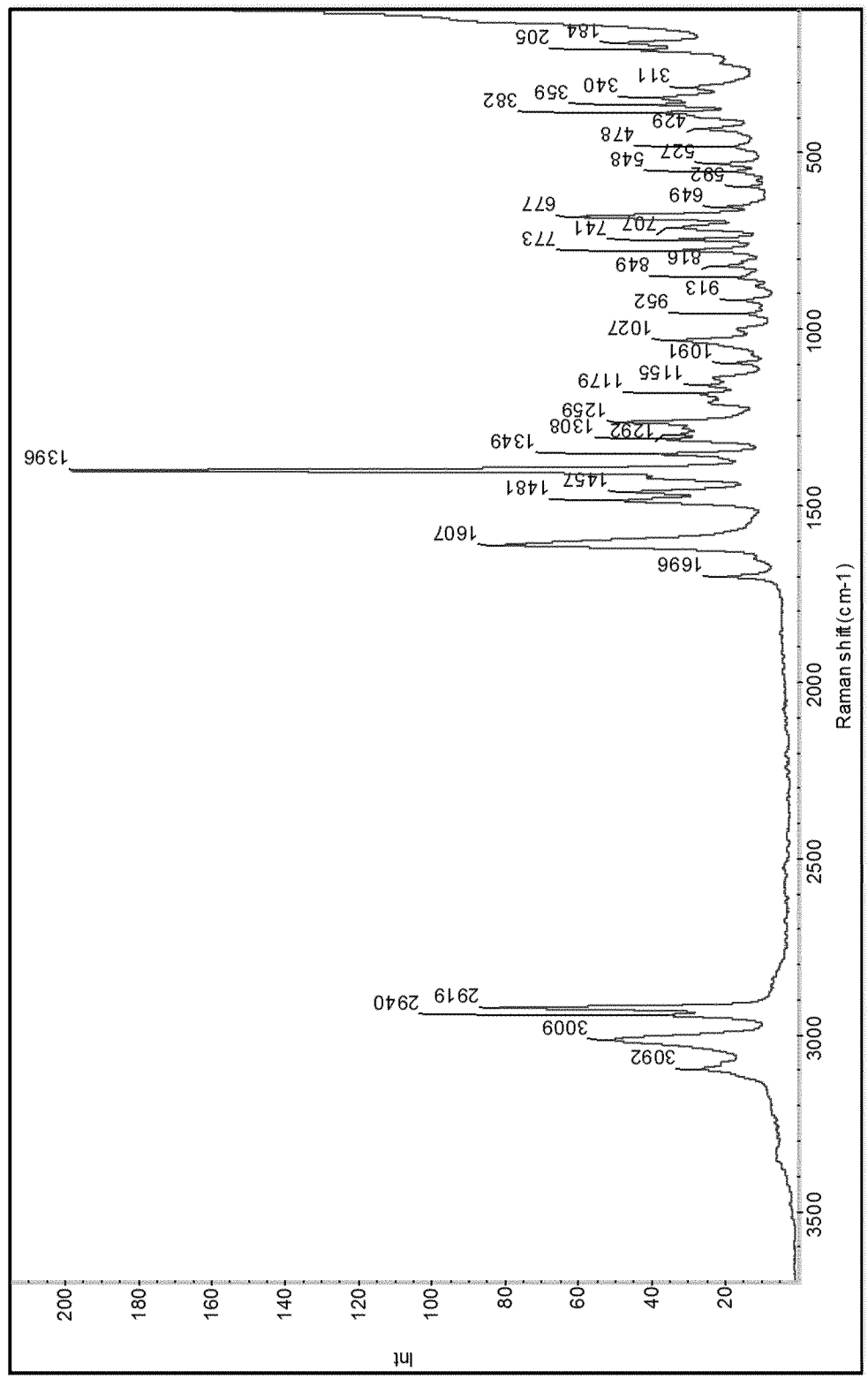
FIG. 7: FT-Raman spectrum of Lenvatinib, form DMSO-2

FT-Raman analysis returns the spectrum shown in FIG. 7.

Figure 8:
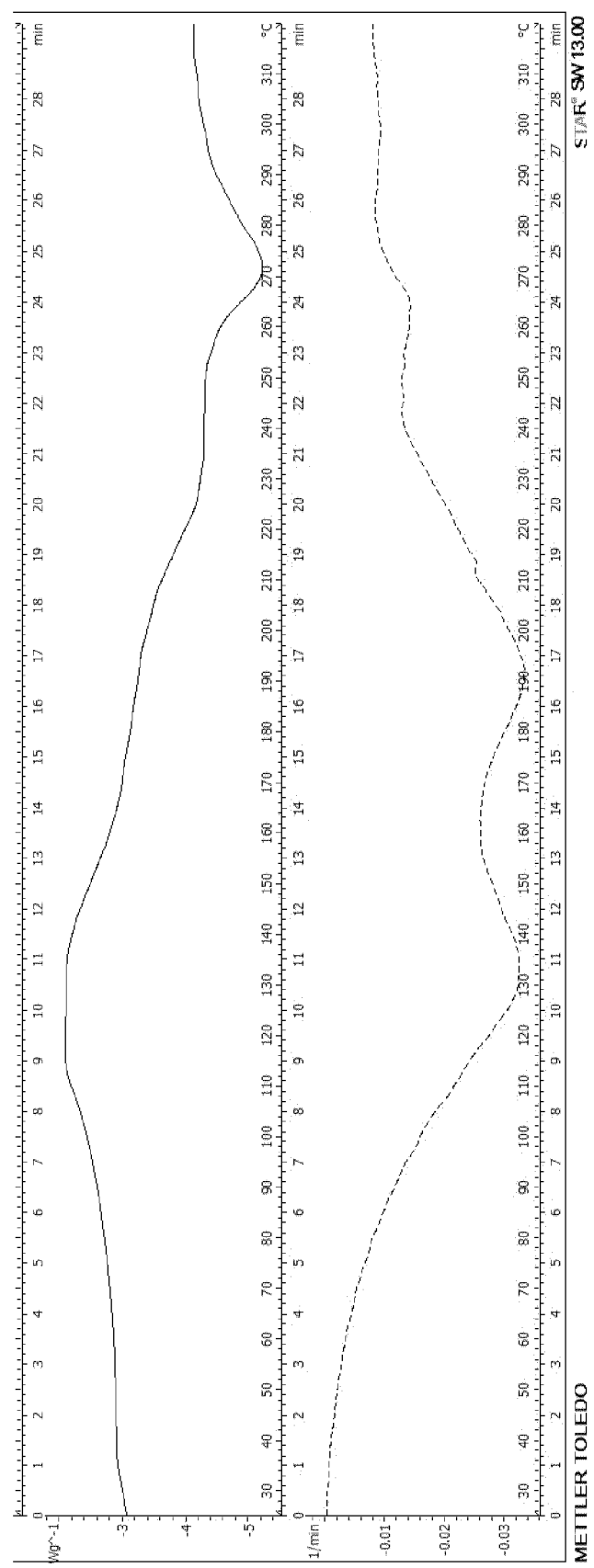
FIG. 8: DSC analysis of Lenvatinib, form DMSO-2

DSC analysis of the Lenvatinib mesylate form DMSO-2, shown in FIG. 8, shows a linear profile with a single event at about 120° C., corresponding to the loss of water and the decomposition occurs without melting.

Figure 9:
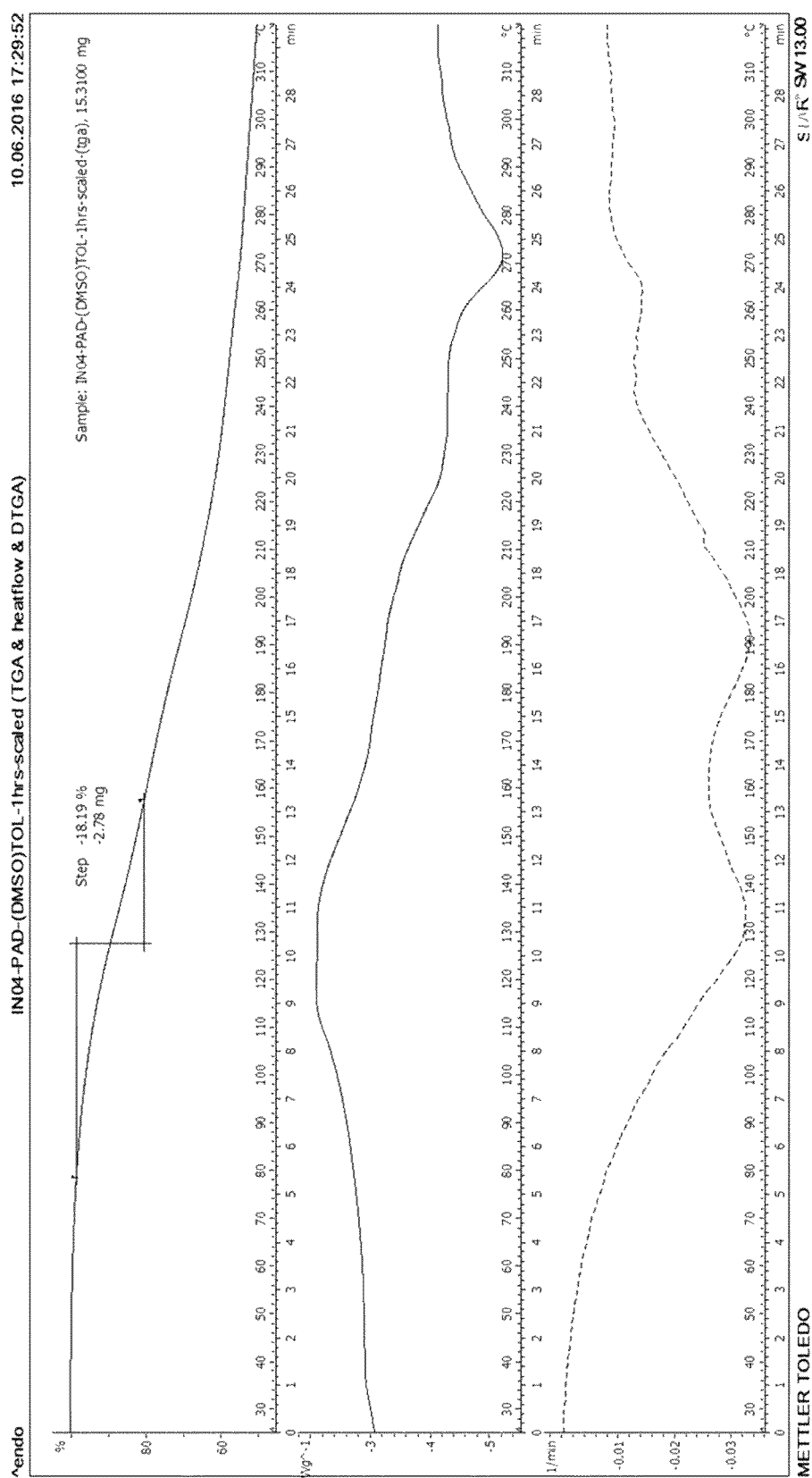
FIG. 9: TGA analysis of Lenvatinib, form DMSO-2
Figure 10:
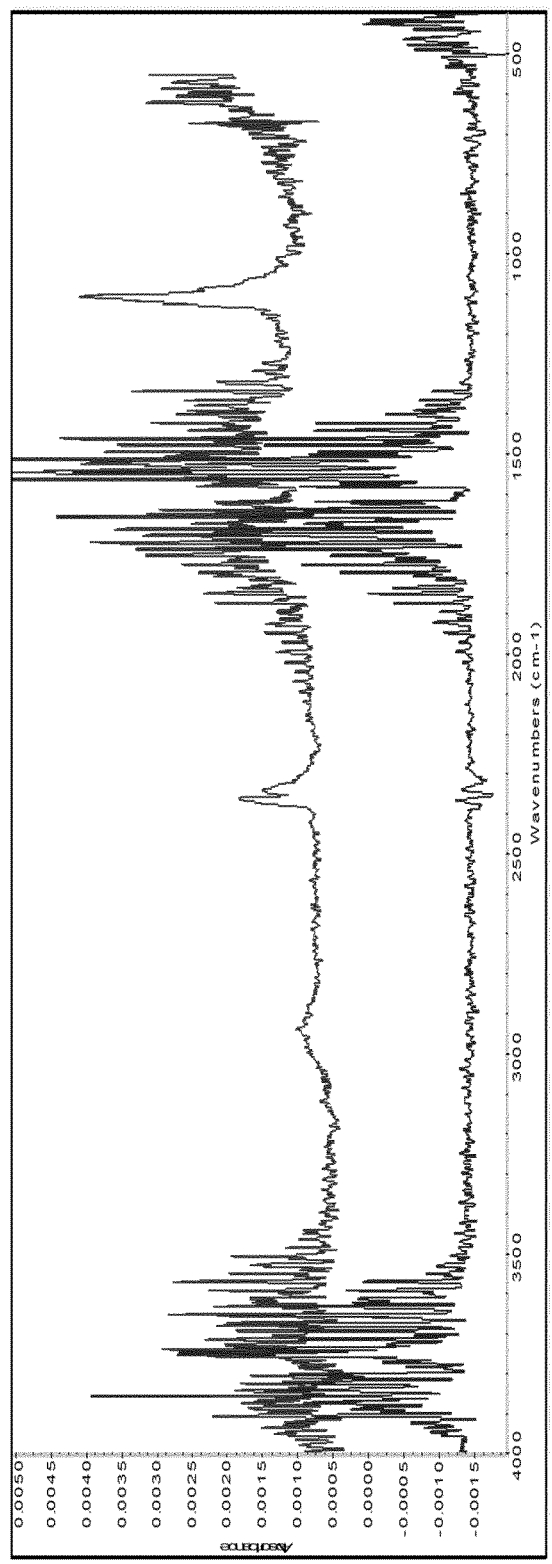
FIG. 10: EGA analysis of Lenvatinib, form DMSO-2

TGA profile showed a broad weight loss up to above 200° C.: The EGA analysis showed the evolution of water (see FIGS. 9 and 10). The significant high weight loss observed suggested the present of other solvents.

Figure 11:
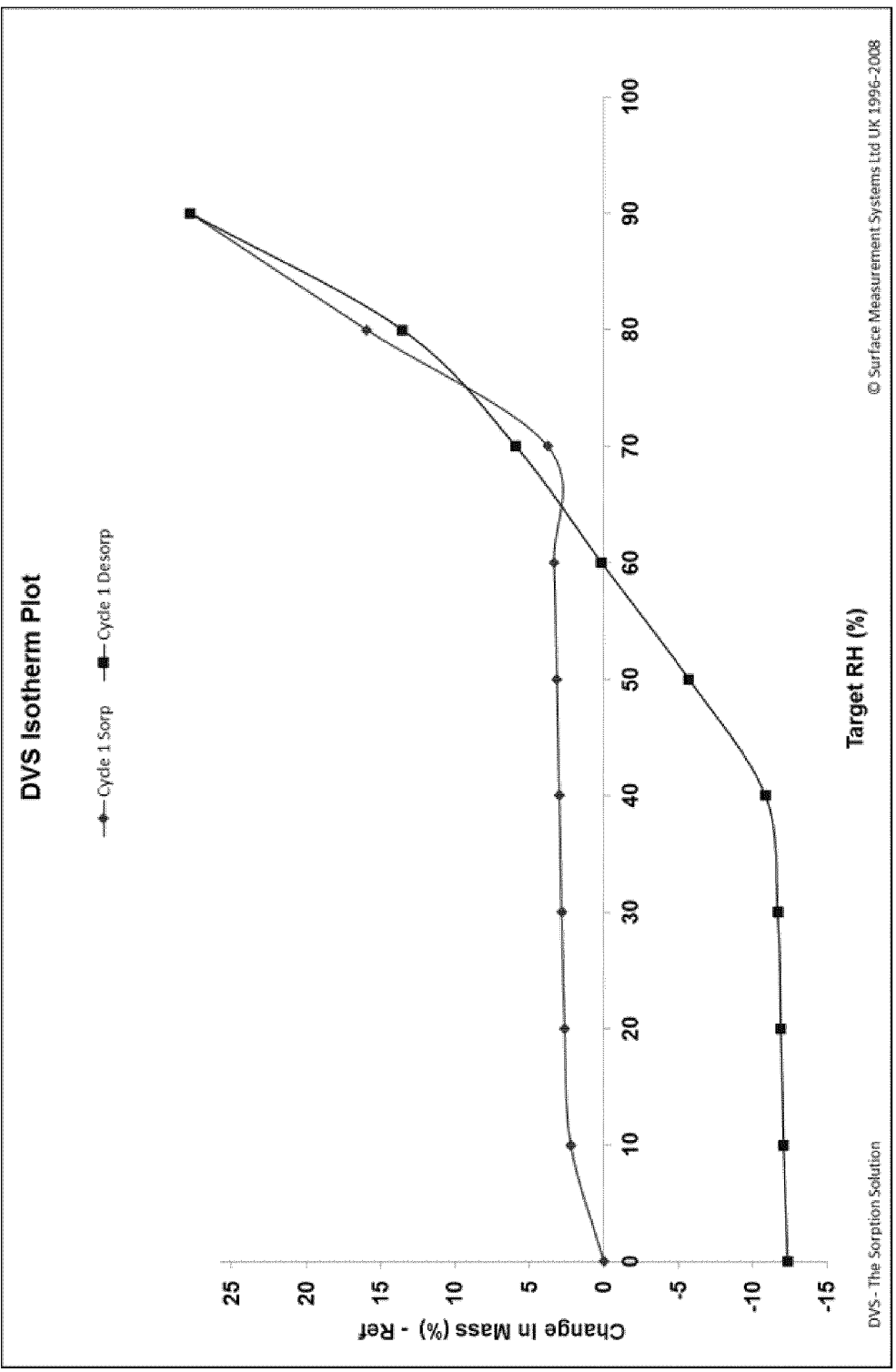
FIG. 11: DVS analysis of Lenvatinib, form DMSO-2

DVS analysis, shown in FIG. 11, reports the percentage change in mass as of the relative humidity change.

The sorption and desorption of water was not reversible. The weight loss of the sample between the start and the end of analysis suggested that water promoted the extrusion of as solvent (the weight loss of 12.34% is compatible with the loss of a 1 mol of DMSO).

Lenvatinib mesylate form DMSO-2 was stored at 60° C. and 75% RH for three days.

Example 3: ACA-1 Form

Lenvatinib Mesylate (10-100 mg) was dissolved in acetic acid (1-10 mL), at a temperature ranging from room temperature to the boiling point of the solvent, to give a solution. The solution was filtered and left to evaporate at 40-80° C. at room pressure in a vial. After three or more days the dry powder was recovered from the vial.

The solid was recovered in a yield ~99% and high level of chemical purity (>99.5%)

Figure 12:
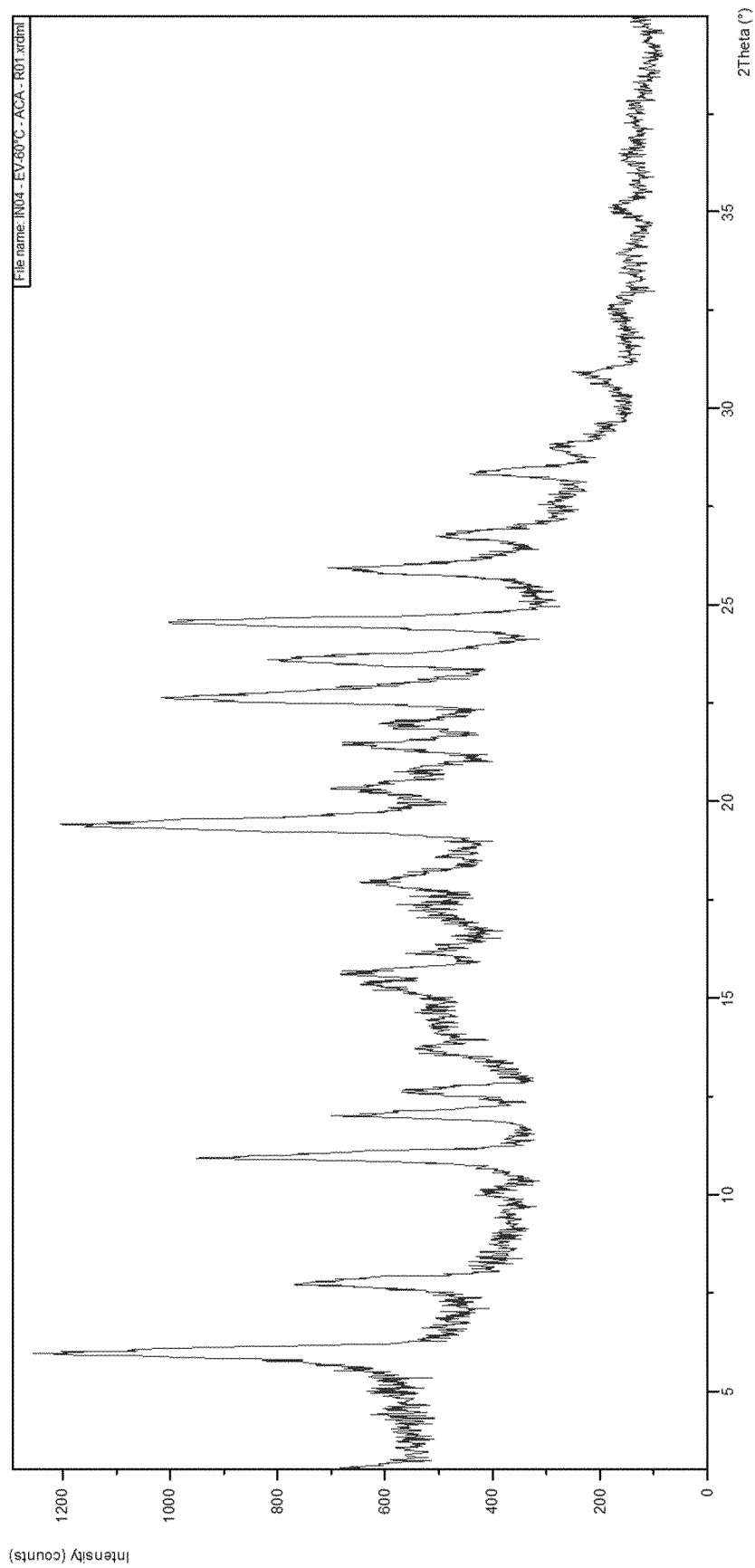
FIG. 12: XRPD spectrum of Lenvatinib, form ACA-1

The new form ACA-1 is a solvate crystal form characterized by the XRPD spectrum shown in FIG. 12. Main peaks at 2theta±0.3 degrees are: 5.9, 7.7, 10.9, 11.9, 12.6, 19.4, 22.6, 23.6, 24.5, 25.9, 26.7.

Table 3 below shows the significant peaks of the spectrum.

TABLE 3

XRPD peak list

| Pos. [°2Th.] | Height [cts] | FWHM [°2Th.] | d-spacing [Å] | Rel. Int. [%] |
| --- | --- | --- | --- | --- |
| 5.9675 | 678.70 | 0.1171 | 14.81073 | 97.27 |
| 7.7192 | 355.59 | 0.1171 | 11.45318 | 50.96 |
| 10.0603 | 45.24 | 0.2676 | 8.79263 | 6.48 |
| 10.9027 | 509.55 | 0.0502 | 8.11507 | 73.03 |
| 11.9794 | 287.64 | 0.0836 | 7.38802 | 41.22 |
| 12.5944 | 188.77 | 0.2342 | 7.02859 | 27.05 |
| 13.7300 | 135.54 | 0.2007 | 6.44974 | 19.43 |
| 15.6097 | 223.70 | 0.1338 | 5.67702 | 32.06 |
| 16.1897 | 78.19 | 0.2007 | 5.47493 | 11.21 |
| 17.1620 | 64.01 | 0.2676 | 5.16688 | 9.17 |
| 17.8466 | 149.98 | 0.2676 | 4.97019 | 21.49 |
| 19.3815 | 697.75 | 0.1338 | 4.57992 | 100.00 |
| 20.3435 | 238.68 | 0.1673 | 4.36545 | 34.21 |
| 20.8512 | 101.26 | 0.2007 | 4.26030 | 14.51 |
| 21.4476 | 220.91 | 0.2342 | 4.14316 | 31.66 |
| 22.0163 | 158.48 | 0.2676 | 4.03740 | 22.71 |
| 22.5948 | 545.13 | 0.2676 | 3.93532 | 78.13 |
| 23.5959 | 427.90 | 0.2676 | 3.77059 | 61.33 |
| 24.5324 | 666.15 | 0.1171 | 3.62873 | 95.47 |
| 25.9295 | 373.65 | 0.2342 | 3.43629 | 53.55 |
| 26.7262 | 200.55 | 0.2007 | 3.33563 | 28.74 |
| 28.3633 | 202.52 | 0.2342 | 3.14672 | 29.02 |
| 29.0095 | 87.47 | 0.2007 | 3.07808 | 12.54 |
| 30.9100 | 76.05 | 0.2007 | 2.89302 | 10.90 |
| 32.5188 | 33.29 | 0.5353 | 2.75348 | 4.77 |
| 35.1122 | 49.25 | 0.3346 | 2.55582 | 7.06 |
| 36.3809 | 26.21 | 0.4015 | 2.46955 | 3.76 |
| 37.6634 | 13.80 | 0.8029 | 2.38836 | 1.98 |

FT-Raman analysis returns the spectrum shown in FIG. 13. The spectrum reports the characteristic bands of form ACA-1.

Figure 14:
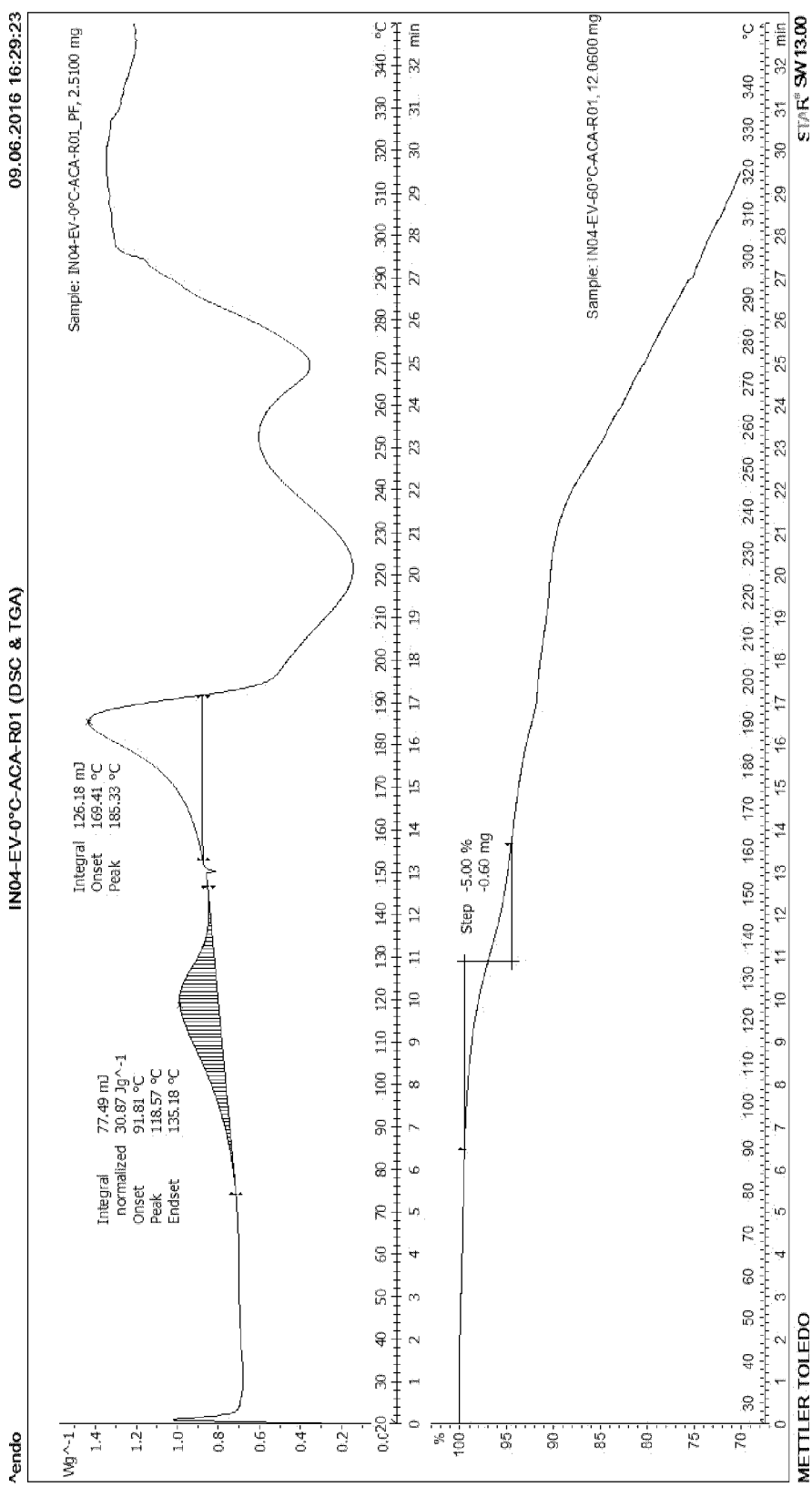
FIG. 14: DSC analysis of Lenvatinib, form ACA-1.

DSC analysis, shown in FIG. 14, highlights a broad endothermic peak approx. at 118° C. (onset=91.2° C.), associated to the loss of acetic acid, and then a second endothermic peak approx. at 185° C. (onset=169.4° C.), associated to the melting/decomposition of the sample.

Figure 15:
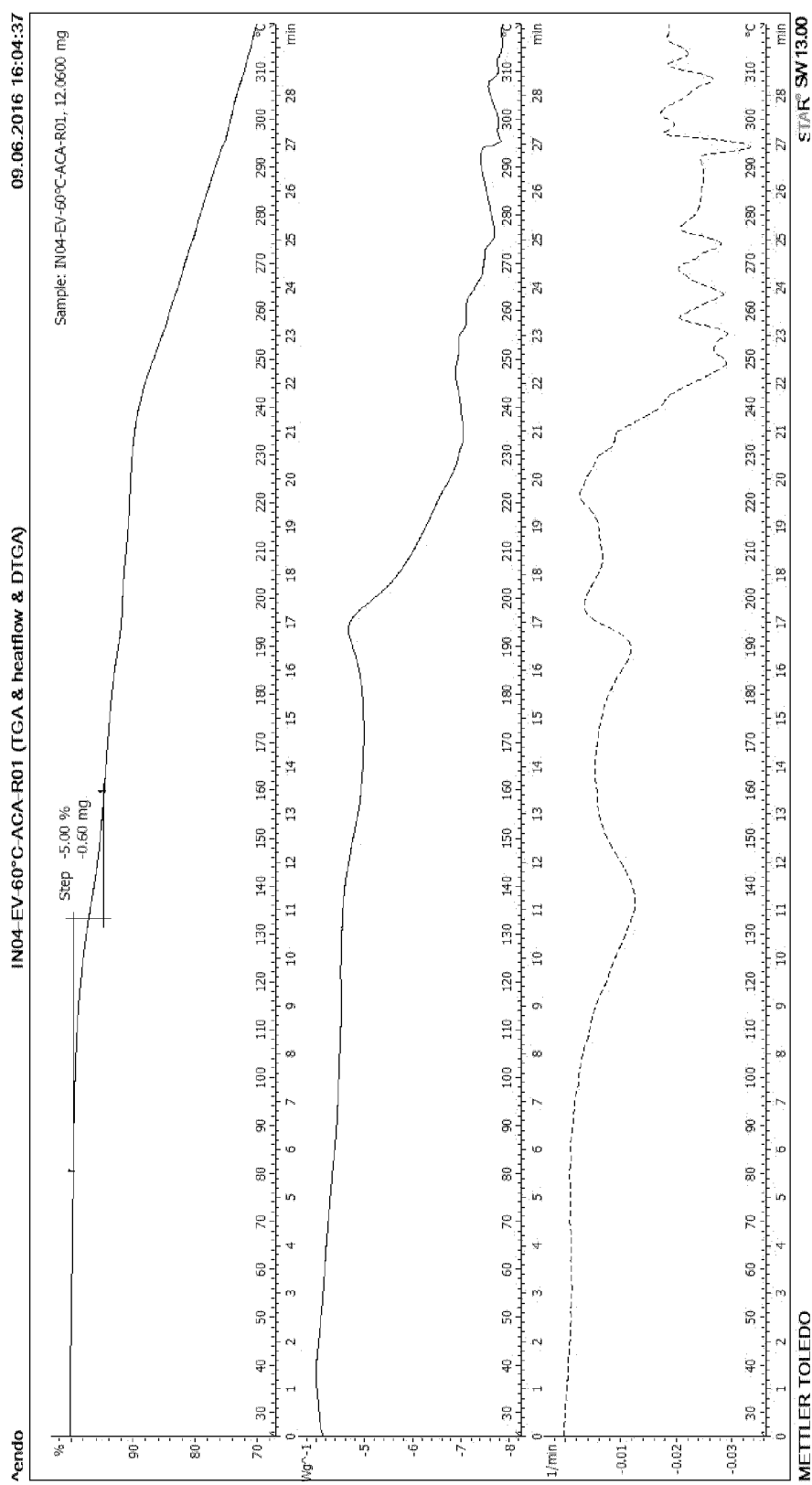
FIG. 15: TGA analysis of Lenvatinib, form ACA-1.
Figure 16:
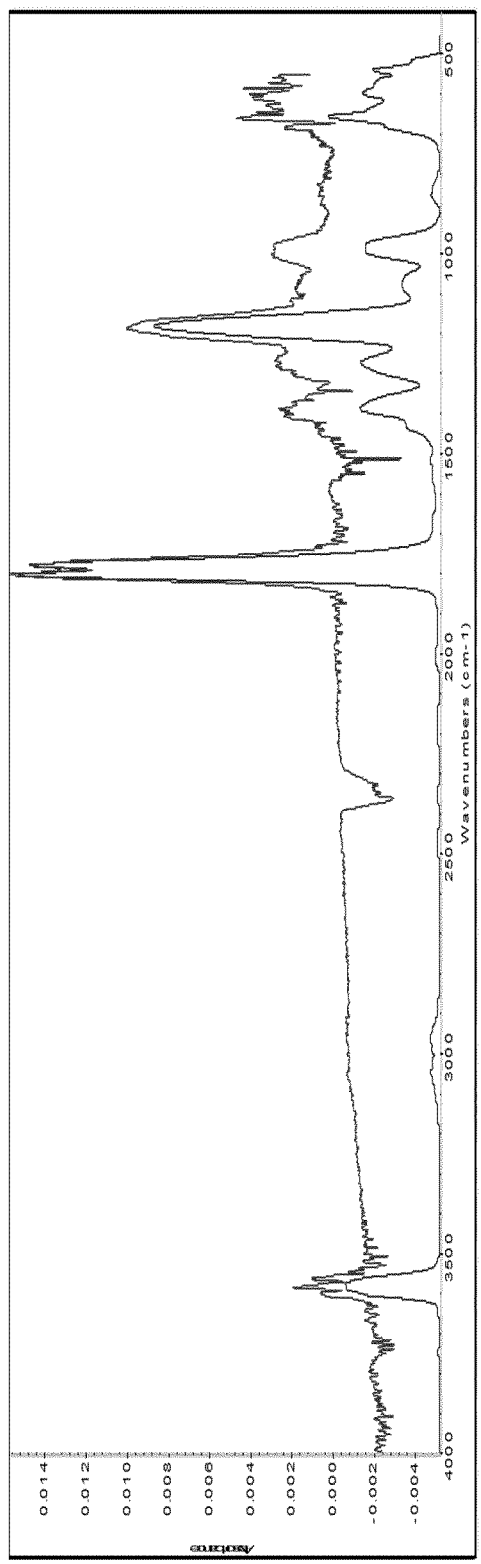
FIG. 16: EGA analysis of Lenvatinib, form ACA-1

The TGA analysis, shown in FIG. 15, highlights a first weight loss of 5.0%, between approx. 90 and 160° C., associated to the loss of 0.5 mol. of acetic acid (as confirmed by EGA analysis FIG. 16) and then two weight losses of acetic acid during the melting/decomposition of the sample, potentially associated to the loss of the solvent mechanically trapped in the solid powder.

Example 4: ACA-1 HT DRY Form

The Lenvatinib mesylate ACA-1 HT DRY of the invention is an anhydrous crystal form which is obtained by heating a sample of the ACA-1 form in an oven at a temperature from 80 to 160° C. and a pressure from 1 to $10^{-2}$ atm.

Figure 17:
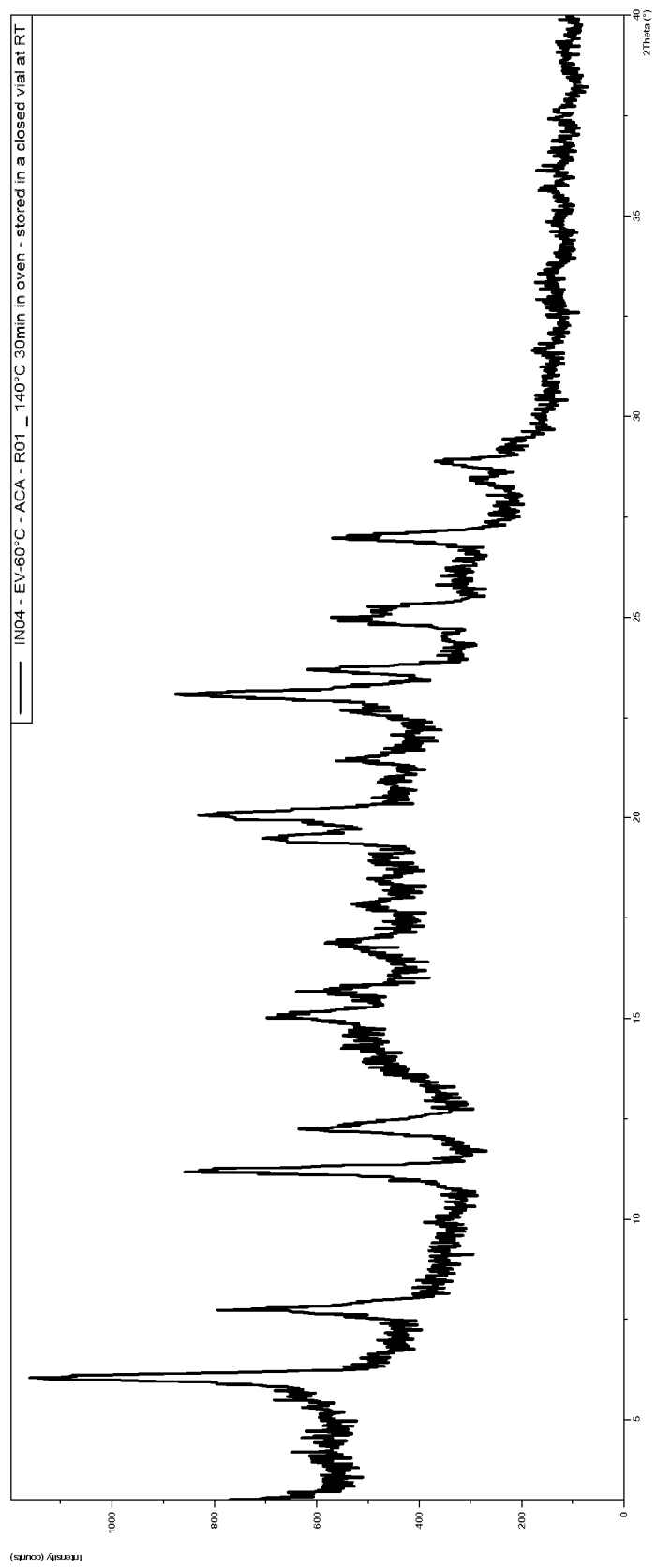
FIG. 17: XRPD spectrum of Lenvatinib, form ACA-1 HT DRY

The solid was recovered in a yield ~99% and high level of chemical purity (>99.5%). The new crystal form ACA-1 HT DRY is characterized by the XRPD spectrum shown in FIG. 17. Main peaks at 2theta±0.3 degrees are: 6.0, 7.7, 11.2, 13.6, 19.4, 20.0, 23.1, 26.9.

Table 4 below shows the significant peaks of the spectrum.

TABLE 4

XRPD peak list

| Pos. [°2Th.] | Height [cts] | FWHM [°2Th.] | d-spacing [Å] | Rel. Int. [%] |
| --- | --- | --- | --- | --- |
| 6.0270 | 655.37 | 0.0836 | 14.66460 | 100.00 |
| 7.7501 | 350.27 | 0.1338 | 11.40758 | 53.45 |
| 11.1820 | 532.12 | 0.0836 | 7.91302 | 81.19 |
| 12.2127 | 285.80 | 0.0836 | 7.24741 | 43.61 |
| 13.6491 | 73.43 | 0.4015 | 6.48778 | 11.20 |
| 15.0621 | 254.99 | 0.2342 | 5.88217 | 38.91 |
| 15.6654 | 155.17 | 0.1673 | 5.65698 | 23.68 |
| 16.8966 | 135.27 | 0.1004 | 5.24743 | 20.64 |
| 17.8266 | 77.24 | 0.2676 | 4.97571 | 11.79 |
| 18.9727 | 36.96 | 0.2007 | 4.67766 | 5.64 |
| 19.4482 | 244.27 | 0.2007 | 4.56436 | 37.27 |
| 20.0429 | 369.02 | 0.2342 | 4.43024 | 56.31 |
| 21.4394 | 113.38 | 0.1338 | 4.14472 | 17.30 |
| 23.0823 | 497.56 | 0.1506 | 3.85330 | 75.92 |
| 23.6943 | 258.69 | 0.1673 | 3.75514 | 39.47 |
| 24.9569 | 219.93 | 0.1673 | 3.56795 | 33.56 |
| 25.2778 | 155.38 | 0.1338 | 3.52338 | 23.71 |
| 26.9899 | 293.07 | 0.2007 | 3.30364 | 44.72 |
| 28.8555 | 174.53 | 0.1171 | 3.09416 | 26.63 |
| 31.6848 | 30.62 | 0.2007 | 2.82403 | 4.67 |
| 33.5104 | 33.25 | 0.4015 | 2.67424 | 5.07 |
| 35.6614 | 40.96 | 0.2007 | 2.51771 | 6.25 |
| 37.5763 | 27.11 | 0.4015 | 2.39370 | 4.14 |

Figure 18:
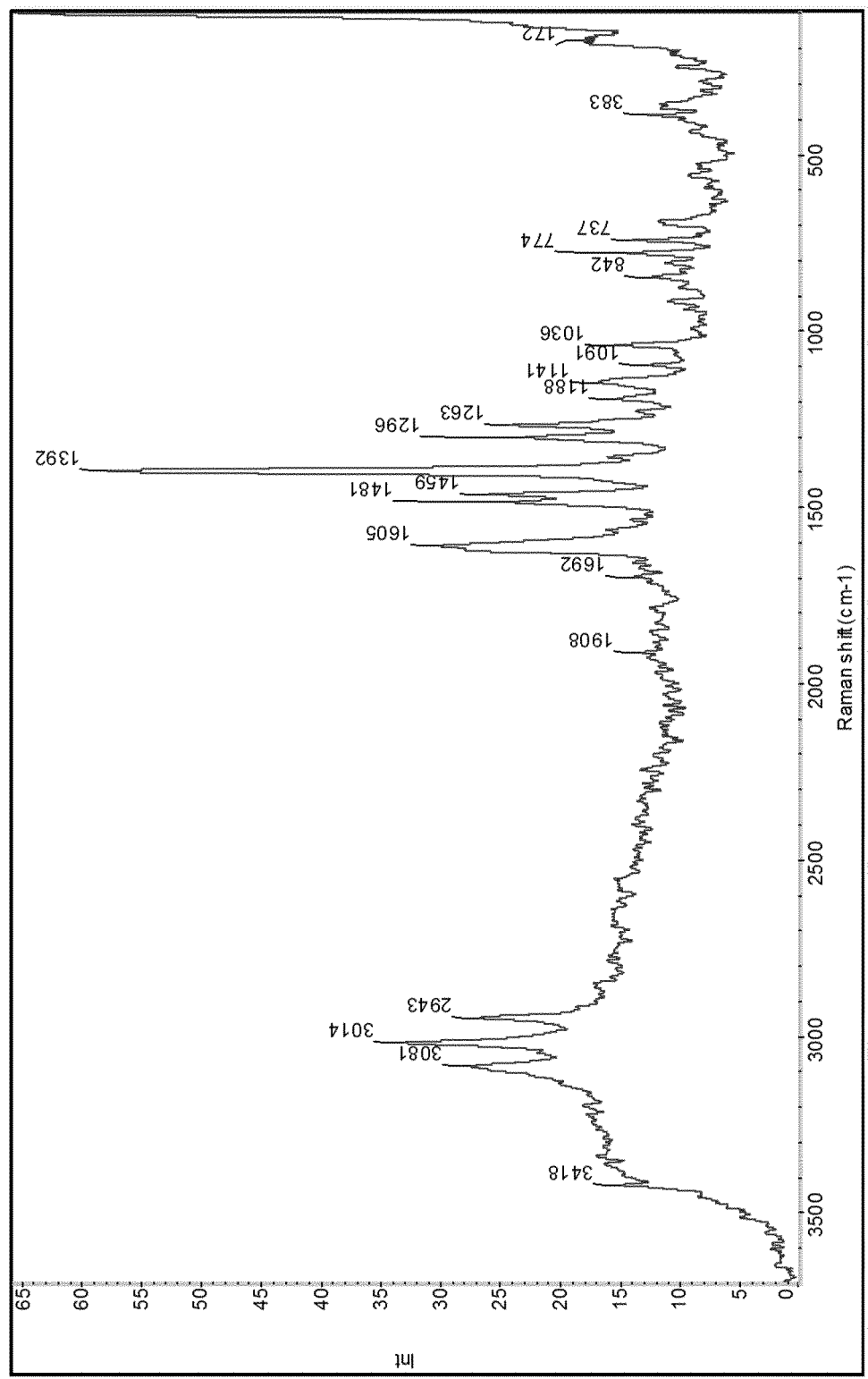
FIG. 18: FT-Raman spectrum of Lenvatinib, form ACA-1 HT DRY.

FT-Raman analysis returns the spectrum shown in FIG. 18. The spectrum reports the characteristic bands of form ACA-1 HT DRY.

Figure 19:
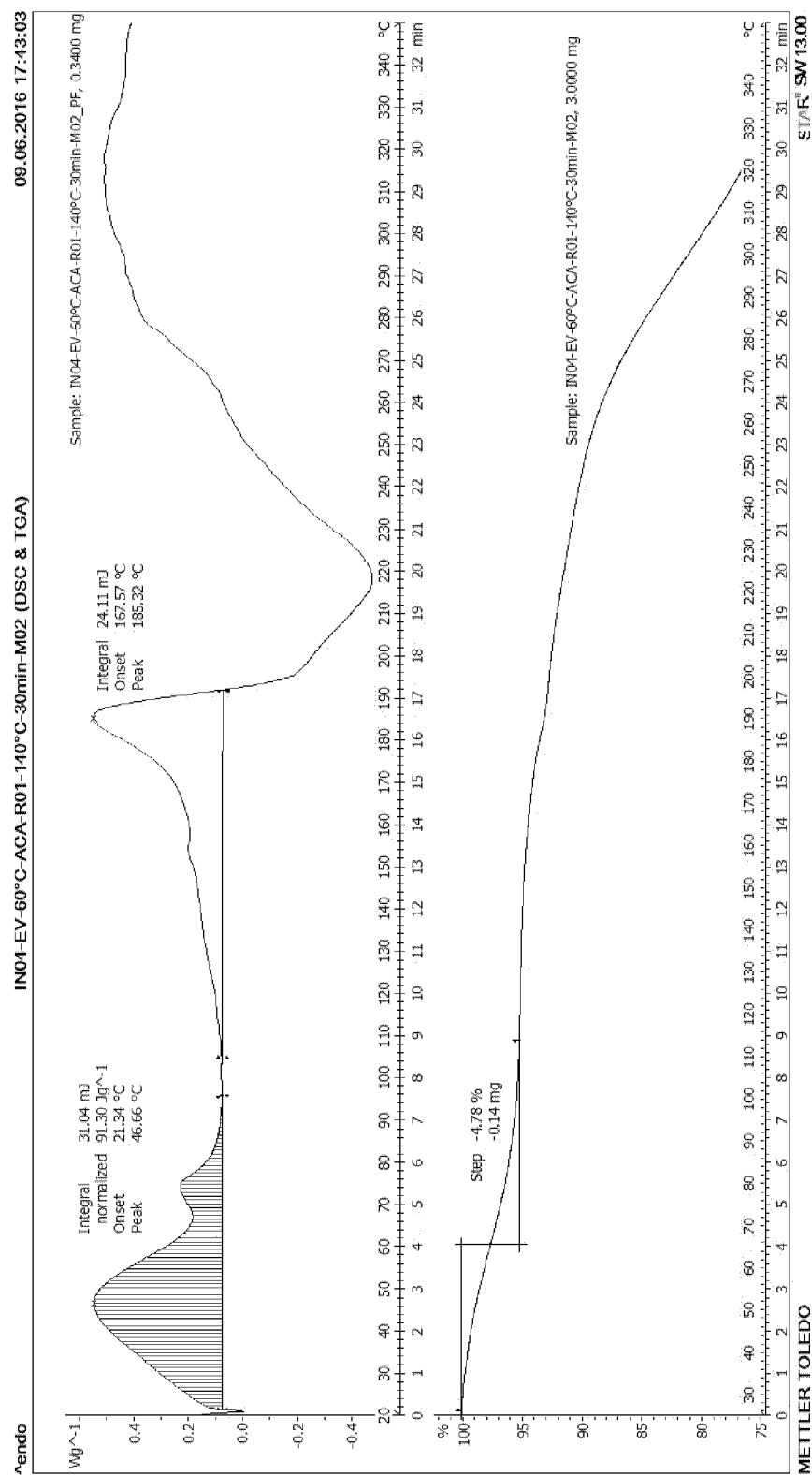
FIG. 19: DSC analysis of Lenvatinib, form ACA-1 HT DRY.

DSC analysis, shown in FIG. 19, highlights a first endothermic event (peak approx. at 47° C.) associated to the evaporation of water, and an endothermic peak at 185° C. (onset=167.6° C.) associated to the melting/decomposition of the sample.

Figure 20:
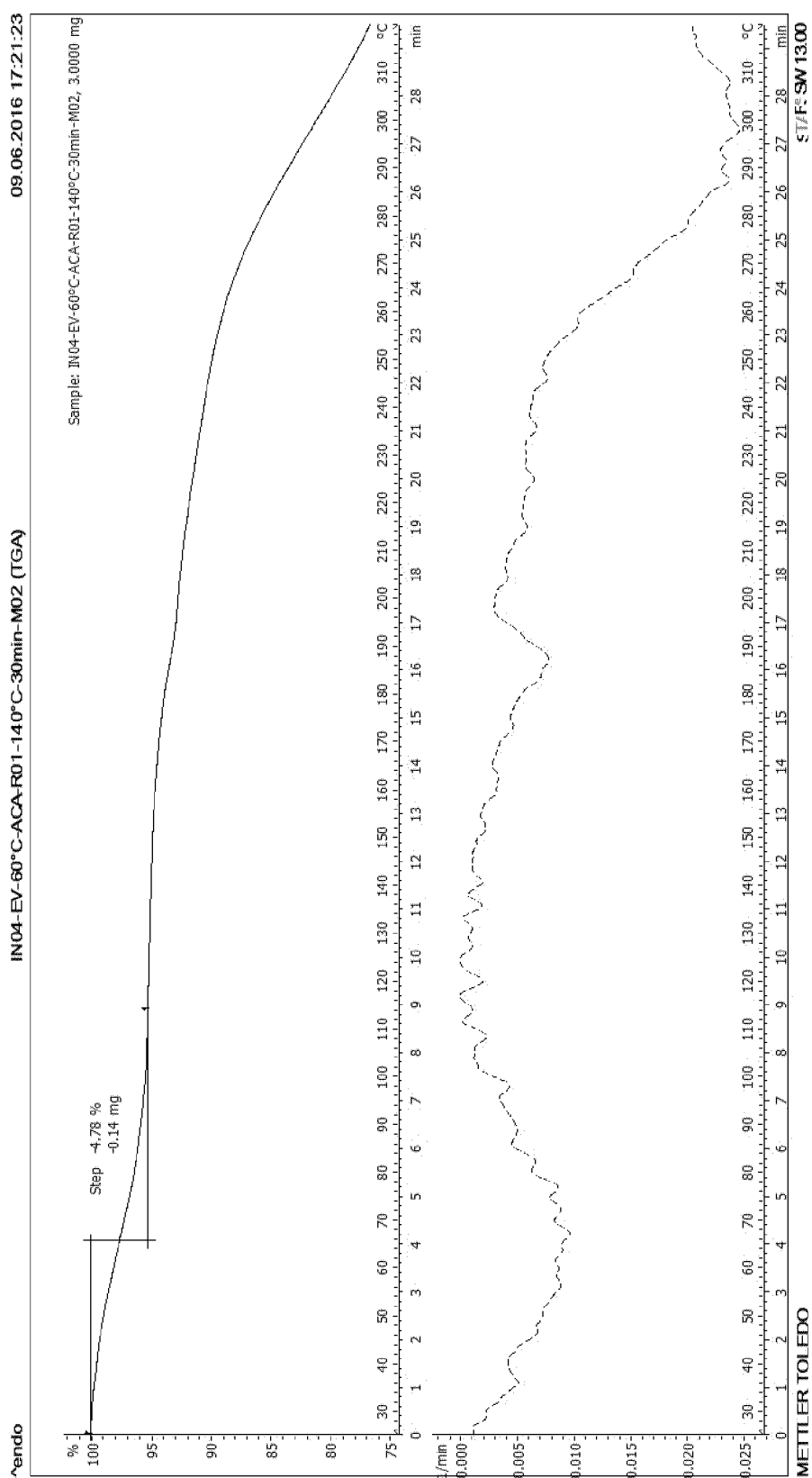
FIG. 20: TGA analysis of Lenvatinib, form ACA-1 HT DRY
Figure 21:
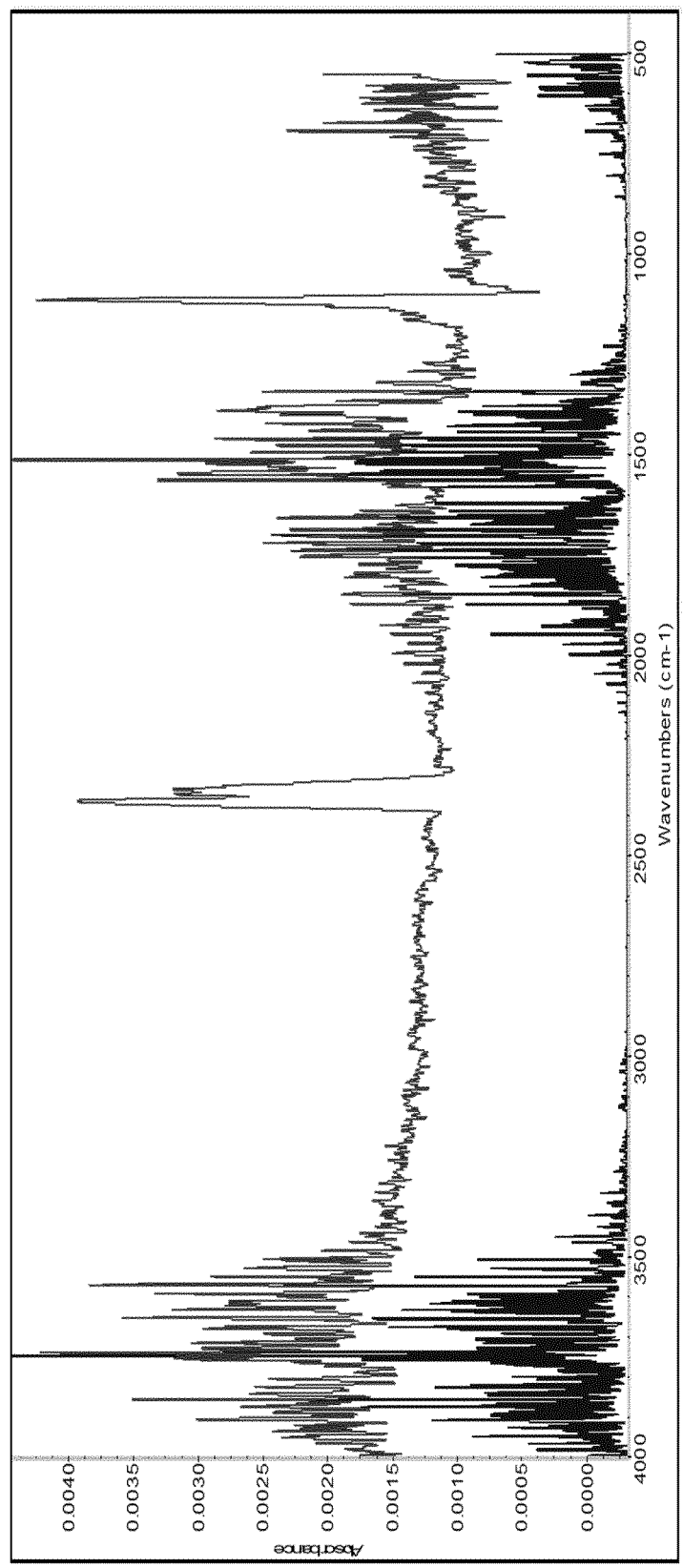
FIG. 21: EGA analysis of Lenvatinib, form ACA-1 HT DRY

The TGA analysis, shown in FIG. 20, highlights an initial weight loss of 4.8%, between approx. 25 and 115° C., reasonably associated to the evaporation of adsorbed water (confirmed by EGA analysis FIG. 21).

Figure 22:
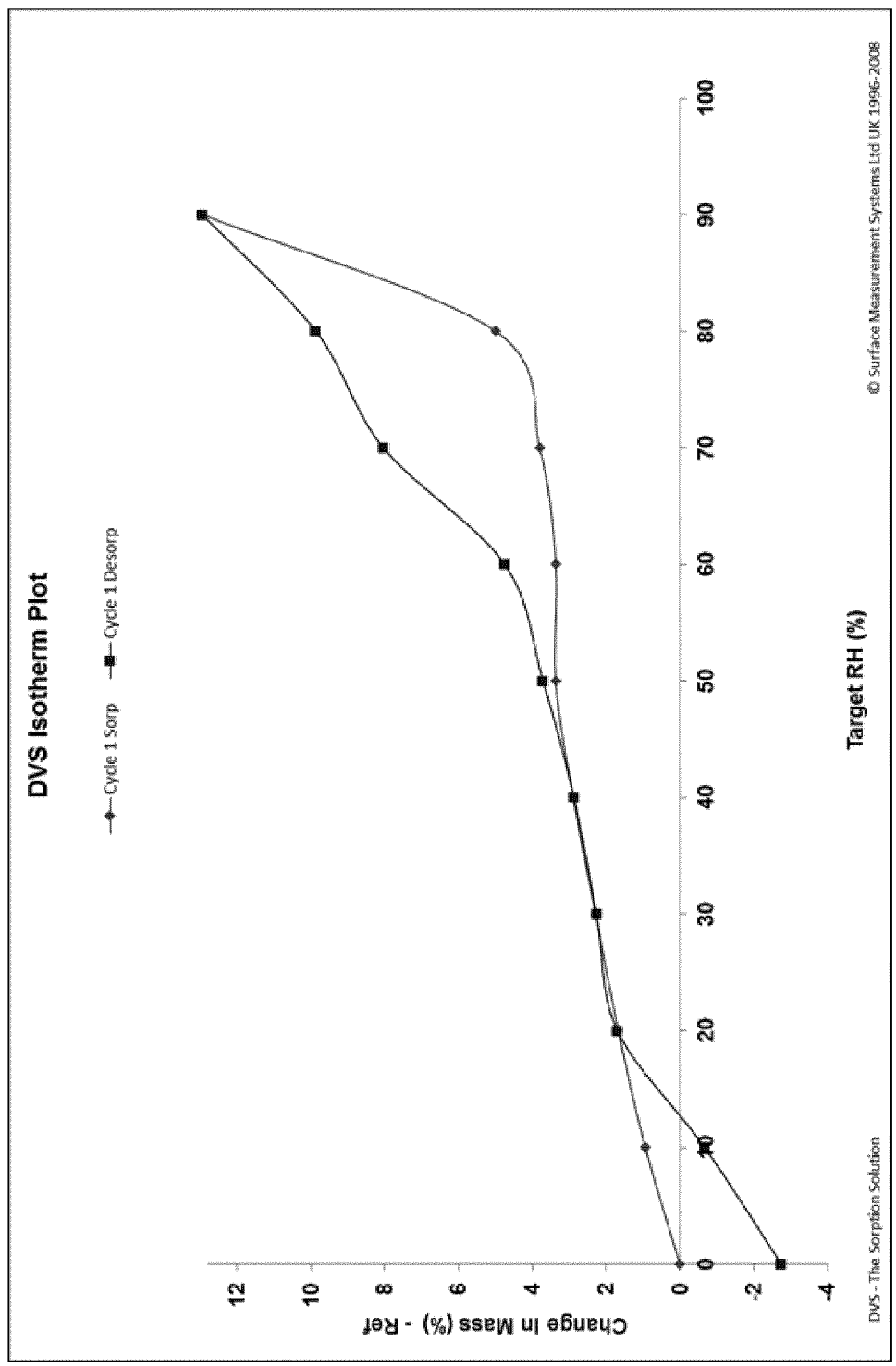
FIG. 22: DVS analysis of Lenvatinib, form ACA-1 HT DRY

The DVS analysis, shown in FIG. 22, reports the percentage change in mass as function of the relative humidity change.

The sorption and desorption of water was not very reversible and the analysis evidenced a small event (probably associated to molecular rearrangements of the API).

The sample recovered at the end of DVS analysis was analyzed by XRPD: its diffractogram was quite amorphous but its crystal structure did not change.

Example 5: CHF-1 Form

A) Lenvatinib Mesylate (100-1000 mg) in an anhydrous form was suspended in chloroform (2-10 mL) and stirred for 1-30 days at a temperature from room temperature to the boiling point of chloroform.

The suspension was recovered under vacuum.

B) Lenvatinib Mesylate (50-100 mg) was dissolved/suspended in acetic acid (100-200 μL), at a temperature ranging from room temperature to the boiling point of the solvent, to give a solution/suspension. The solution/suspension was left under stirring (1-16 hours) and then filtered to obtain a clear solution.

Chloroform (0.5-4.0 mL) was added dropwise to the formic acid solution under stirring at a temperature ranging from 10 to 40° C.

After 1-5 days the precipitate was recovered under vacuum and washed with chloroform.

Figure 23:
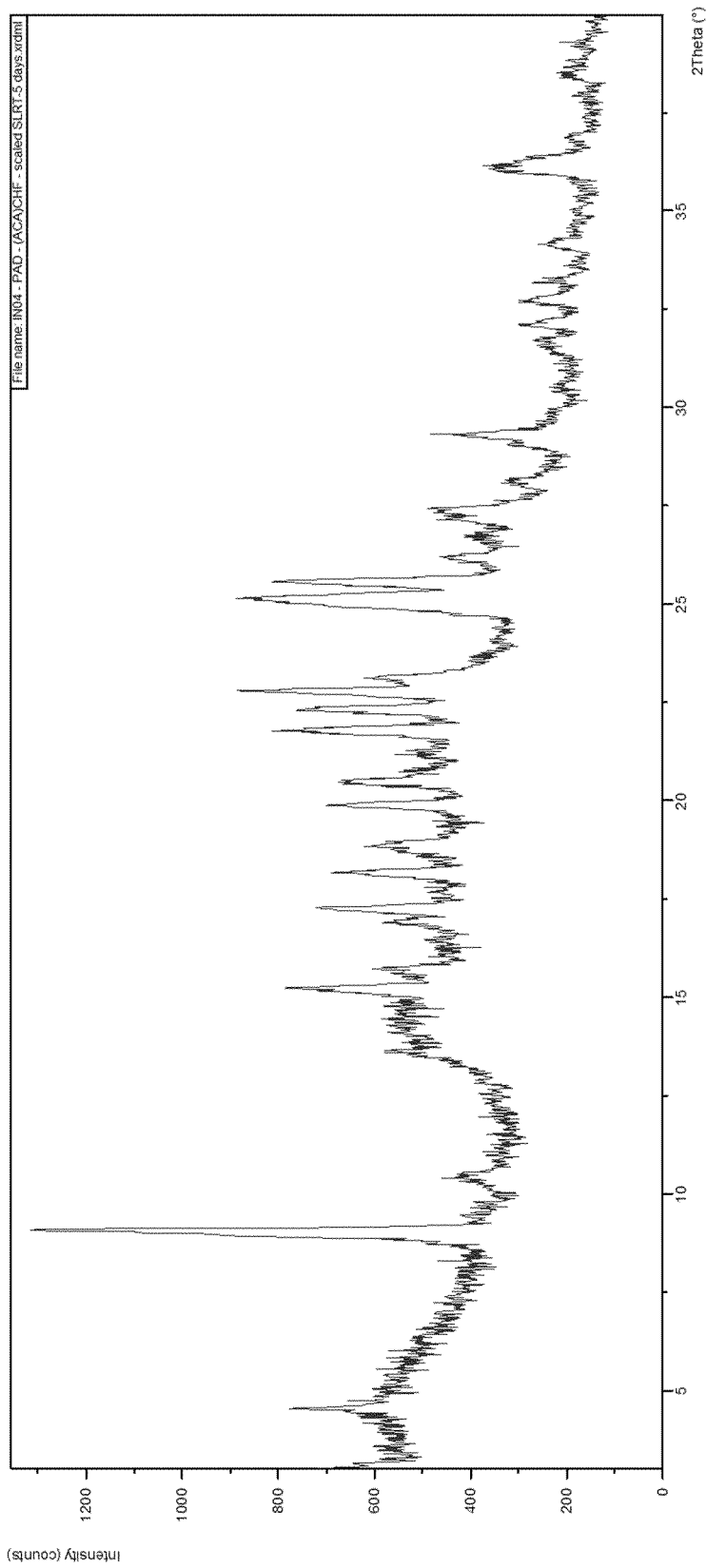
FIG. 23: XRPD spectrum of Lenvatinib, form CHF-1

The new crystal form CHF-1 is characterized by the XRPD spectrum shown in FIG. 23.

Main peaks at 2theta±0.3 degrees are: 4.5, 9.1, 15.7, 16.9, 17.3, 18.2, 18.9, 19.9, 20.5, 21.1, 21.8, 22.4, 22.8, 25.1, 25.6.

Table 5 below shows the significant peaks of the spectrum.

TABLE 5

XRPD peak list

| Pos. [°2Th.] | Height [cts] | FWHM [°2Th.] | d-spacing [Å] | Rel. Int. [%] |
|---|---|---|---|---|
| 4.5317 | 231.81 | 0.0502 | 19.49947 | 24.63 |
| 9.0800 | 941.37 | 0.0836 | 9.73959 | 100.00 |
| 10.4474 | 83.89 | 0.2007 | 8.46772 | 8.91 |
| 13.6044 | 187.54 | 0.1673 | 6.50898 | 19.92 |
| 15.2283 | 363.44 | 0.0669 | 5.81836 | 38.61 |
| 15.7388 | 147.19 | 0.1338 | 5.63073 | 15.64 |
| 16.9025 | 115.41 | 0.1004 | 5.24563 | 12.26 |
| 17.2738 | 263.95 | 0.1338 | 5.13368 | 28.04 |
| 18.1760 | 219.19 | 0.1004 | 4.88085 | 23.28 |
| 18.8898 | 125.23 | 0.1338 | 4.69800 | 13.30 |
| 19.8735 | 263.26 | 0.0836 | 4.46761 | 27.97 |
| 20.4742 | 229.56 | 0.1673 | 4.33789 | 24.39 |
| 21.1878 | 80.34 | 0.2007 | 4.19337 | 8.53 |
| 21.8034 | 349.61 | 0.2007 | 4.07635 | 37.14 |
| 22.3367 | 350.64 | 0.1673 | 3.98022 | 37.25 |
| 22.7851 | 480.34 | 0.1004 | 3.90289 | 51.03 |
| 23.1223 | 253.60 | 0.1004 | 3.84672 | 26.94 |
| 25.1448 | 546.45 | 0.1171 | 3.54172 | 58.05 |
| 25.5781 | 487.93 | 0.1004 | 3.48270 | 51.83 |
| 26.1911 | 142.50 | 0.1673 | 3.40255 | 15.14 |
| 26.7025 | 84.65 | 0.2007 | 3.33855 | 8.99 |
| 27.4179 | 191.40 | 0.1673 | 3.25304 | 20.33 |
| 28.1352 | 64.50 | 0.2007 | 3.17171 | 6.85 |
| 29.3075 | 216.21 | 0.1673 | 3.04746 | 22.97 |
| 31.6745 | 59.36 | 0.3346 | 2.82492 | 6.31 |
| 32.0849 | 96.81 | 0.2007 | 2.78972 | 10.28 |
| 32.7288 | 94.40 | 0.2007 | 2.73629 | 10.03 |
| 33.2522 | 47.13 | 0.2007 | 2.69441 | 5.01 |
| 34.1278 | 72.77 | 0.2342 | 2.62726 | 7.73 |
| 35.9972 | 164.31 | 0.1673 | 2.49499 | 17.45 |
| 36.9065 | 41.47 | 0.1673 | 2.43558 | 4.41 |
| 38.4582 | 59.55 | 0.2007 | 2.34081 | 6.33 |
| 39.2658 | 45.51 | 0.2007 | 2.29451 | 4.83 |

Figure 24:
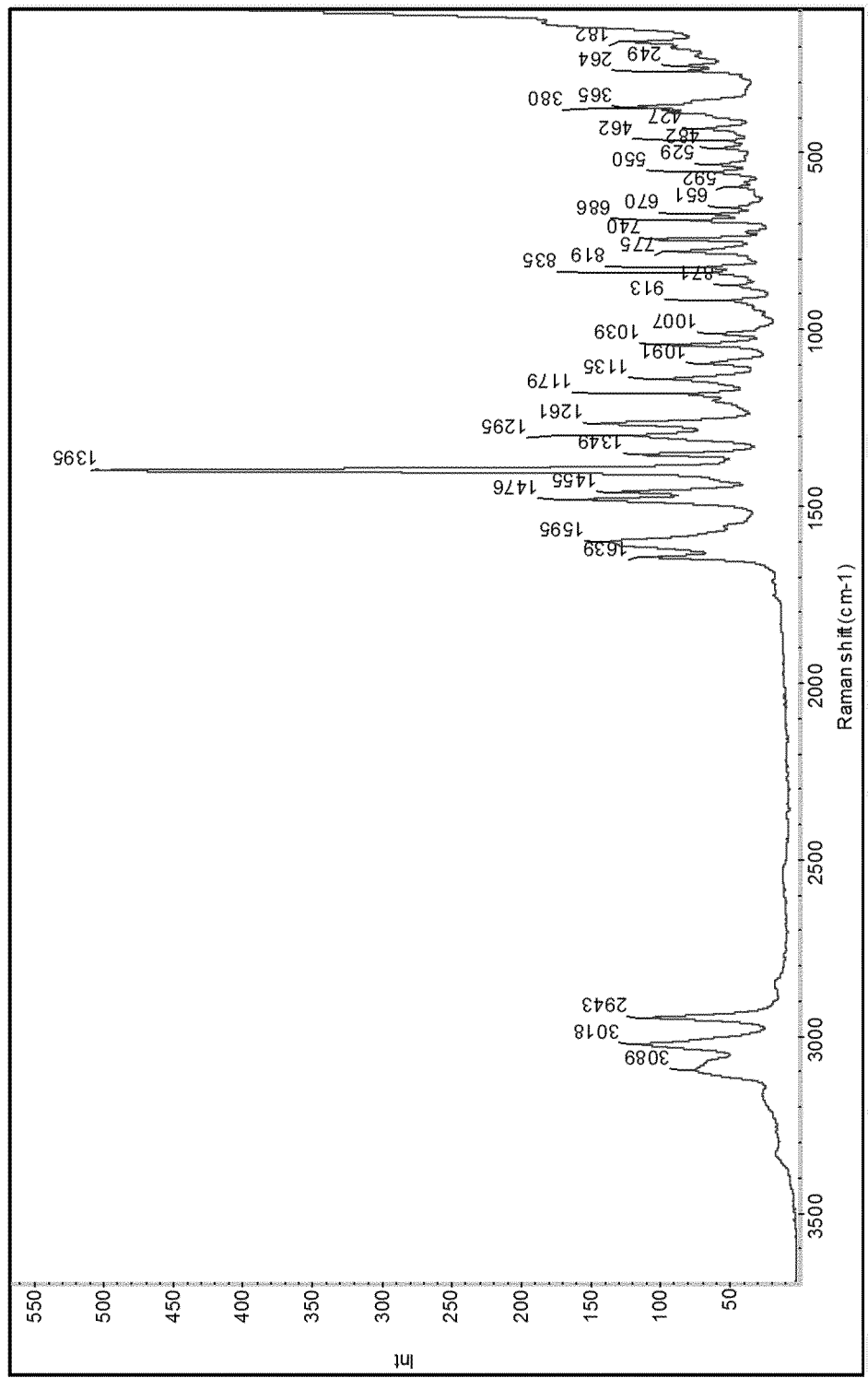
FIG. 24: FT-Raman spectrum of Lenvatinib, form CHF-1

FT-Raman analysis returns the spectrum shown in FIG. 24. The spectrum reports the characteristic bands of form CHF-1.

Figure 25:
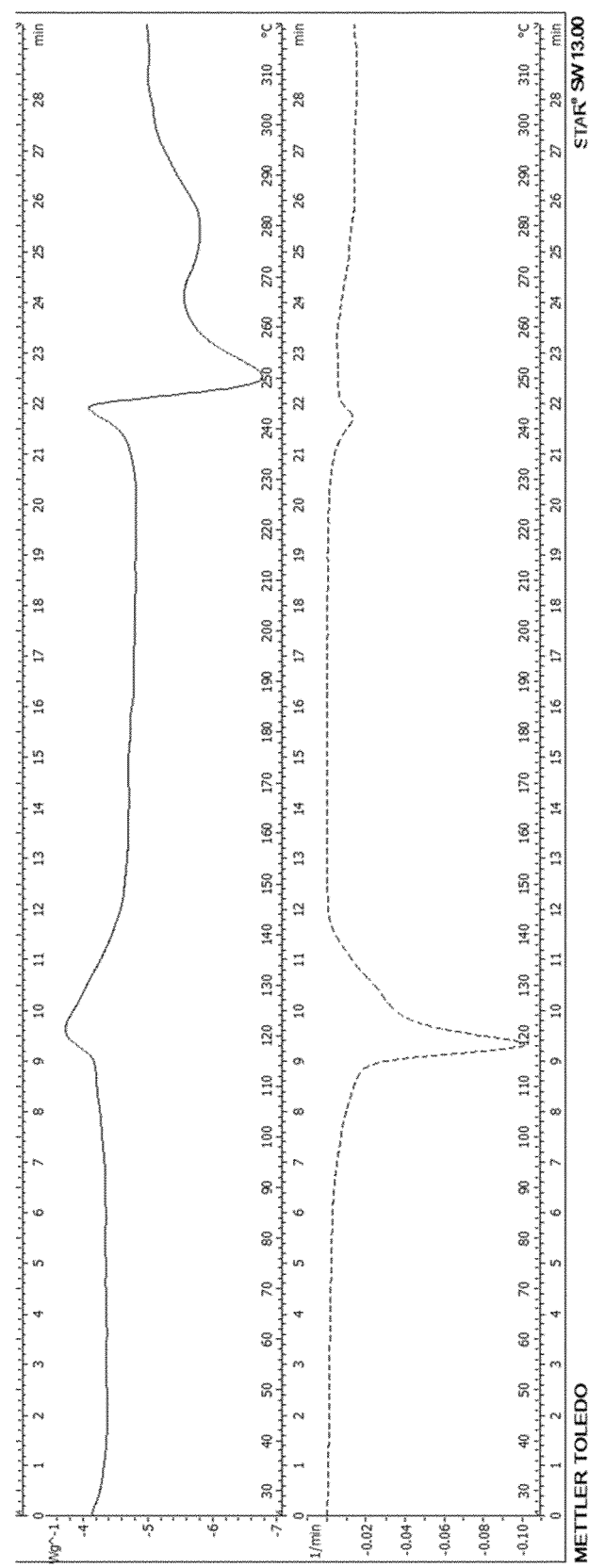
FIG. 25: DSC analysis of Lenvatinib, form CHF-1

DSC analysis, shown in FIG. 25, highlights an endothermic peak during the weight loss at approx. 120° C. and the melting at approx. 240° C.

Figure 26:
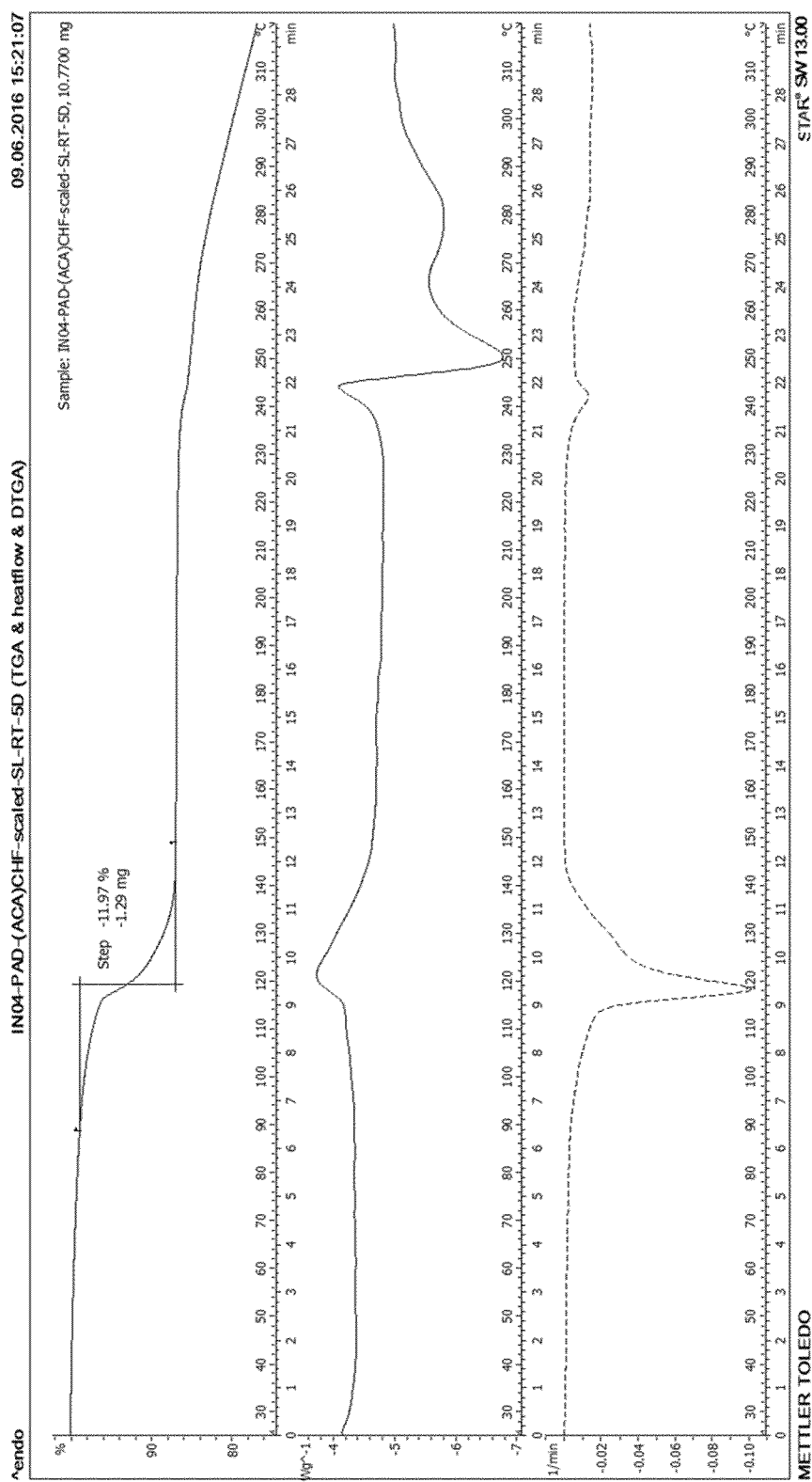
FIG. 26: TGA analysis of Lenvatinib, form CHF-1
Figure 27:
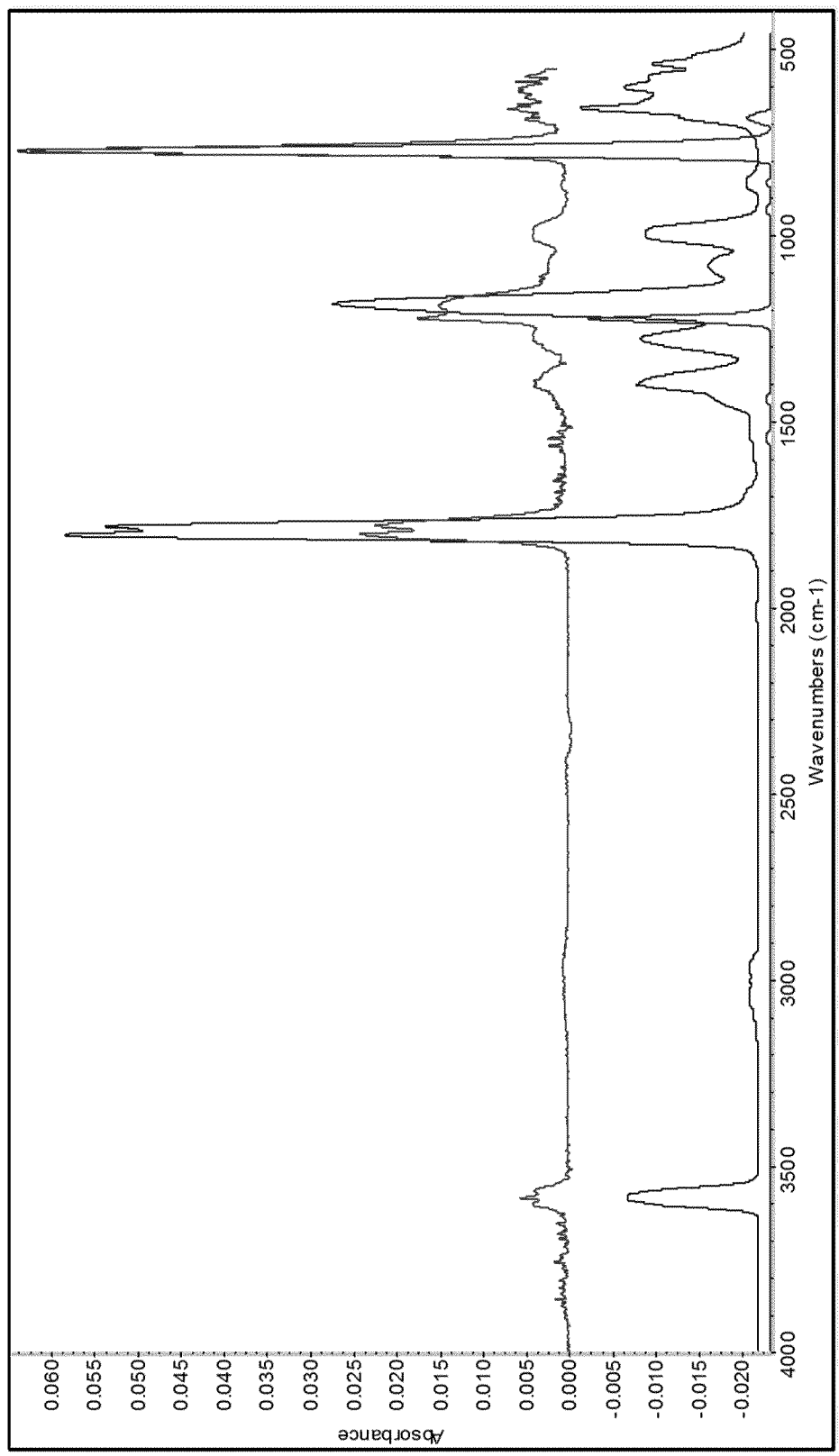
FIG. 27: EGA analysis of Lenvatinib, form CHF-1

The TGA analysis, shown in FIG. 26, highlights a weight loss approx. of 12%, between approx. 90 and 150° C., and then the decomposition of the sample after 230° C. The EG analysis demonstrates that the weight loss was due to the simultaneously loss of acetic acid and chloroform (see FIG. 27).

Example 6 FOA-1

Lenvatinib Mesylate (50-100 mg) was dissolved in formic acid (100-200 μL), at a temperature ranging from room temperature to the boiling point of the solvent, to give a solution. The solution was left under stirring (1-16 hours) and then filtered to obtain a clear solution.

An anti-solvent (0.5-4.0 mL) was added dropwise to the formic acid solution under stirring at a temperature ranging from 10 to 40° C. The anti-solvents used were esters (preferably ethyl formate, ethyl acetate and isopropyl acetate), ethers (preferably THF and TBME), alcohols (preferably ethanol and 2-propanol), chlorinated solvents (preferably chloroform and dichloromethane), ketones (preferably acetone and MEK), and polar aprotic solvents (preferably acetonitrile). After 30-180 minutes the precipitate was recovered under vacuum and washed with a low-boiling anti-solvent.

Figure 28:
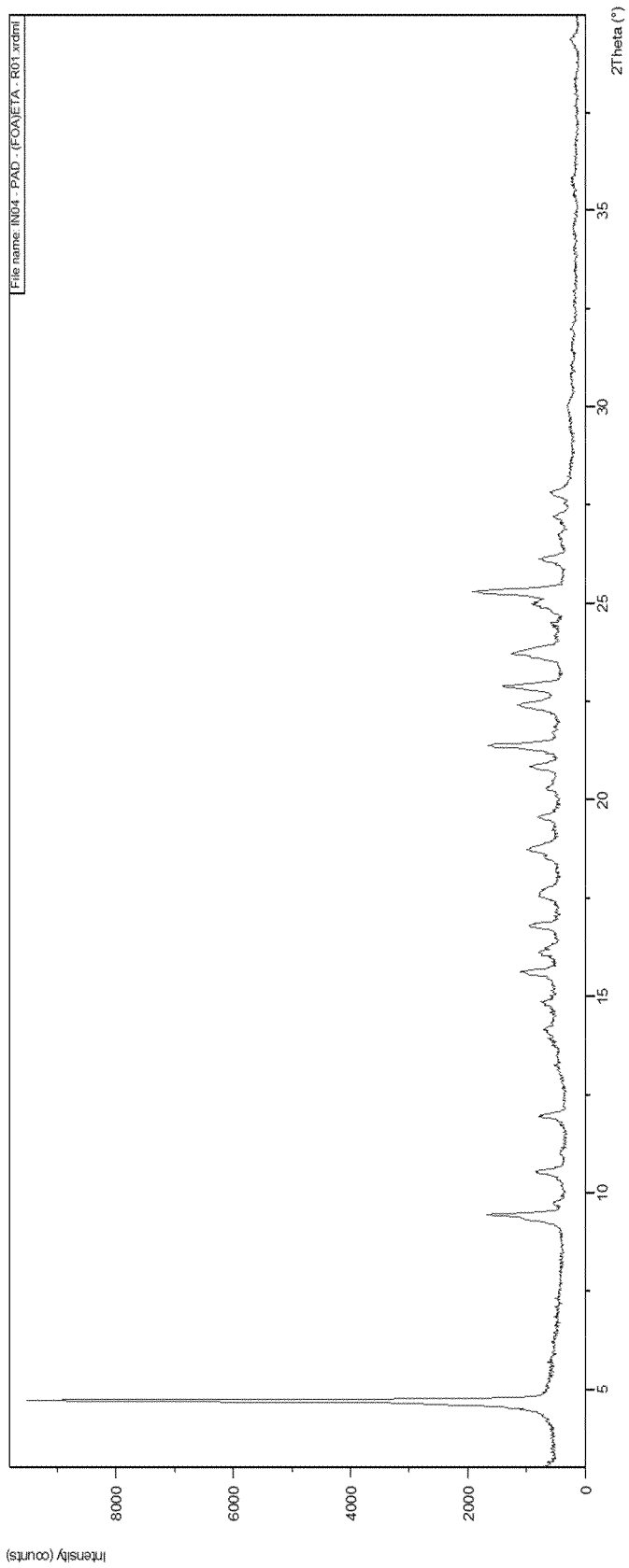
FIG. 28: XRPD spectrum of Lenvatinib, form FOA-1

The Lenvatinib mesylate FOA-1 of the invention is a solvate crystal form characterized by the XRPD spectrum shown in FIG. 28. Main peaks at 2theta±0.3 degrees are: 4.7, 10.5, 11.9, 16.1, 16.8, 17.5, 21.4, 22.4, 22.9, 23.7, 26.1.

Table 6 below shows the significant peaks of the spectrum.

TABLE 6

XRPD peak list

| Pos. [°2Th.] | Height [cts] | FWHM [°2Th.] | d-spacing [Å] | Rel. Int. [%] |
|---|---|---|---|---|
| 4.7056 | 8638.17 | 0.0669 | 18.77925 | 100.00 |
| 9.4334 | 1236.23 | 0.0669 | 9.37550 | 14.31 |
| 9.7391 | 150.90 | 0.0669 | 9.08188 | 1.75 |
| 10.5531 | 443.43 | 0.1004 | 8.38312 | 5.13 |
| 11.0441 | 52.64 | 0.1338 | 8.01150 | 0.61 |
| 11.9195 | 391.67 | 0.0836 | 7.42503 | 4.53 |
| 14.1605 | 175.57 | 0.1338 | 6.25457 | 2.03 |
| 14.8579 | 220.85 | 0.0669 | 5.96256 | 2.56 |
| 15.6284 | 552.32 | 0.1171 | 5.67027 | 6.39 |
| 16.1269 | 259.53 | 0.1004 | 5.49611 | 3.00 |
| 16.7771 | 451.35 | 0.0669 | 5.28455 | 5.23 |
| 17.5530 | 309.73 | 0.1338 | 5.05266 | 3.59 |
| 18.7042 | 449.91 | 0.0836 | 4.74419 | 5.21 |
| 19.5635 | 309.62 | 0.1506 | 4.53771 | 3.58 |
| 20.2838 | 155.01 | 0.1004 | 4.37818 | 1.79 |
| 20.8501 | 423.22 | 0.1171 | 4.26051 | 4.90 |
| 21.3861 | 1092.05 | 0.1171 | 4.15493 | 12.64 |
| 22.4273 | 645.95 | 0.1338 | 3.96434 | 7.48 |
| 22.8760 | 922.21 | 0.1338 | 3.88758 | 10.68 |
| 23.7231 | 817.47 | 0.0669 | 3.75065 | 9.46 |
| 24.4829 | 135.44 | 0.0502 | 3.63596 | 1.57 |
| 24.9629 | 445.68 | 0.1338 | 3.56711 | 5.16 |
| 25.3105 | 1456.27 | 0.1338 | 3.51891 | 16.86 |
| 26.1156 | 386.09 | 0.1338 | 3.41223 | 4.47 |
| 26.7493 | 101.25 | 0.1338 | 3.33281 | 1.17 |
| 27.1948 | 198.26 | 0.0836 | 3.27921 | 2.30 |
| 27.8395 | 307.72 | 0.0669 | 3.20473 | 3.56 |
| 30.0595 | 71.07 | 0.2676 | 2.97291 | 0.82 |
| 31.0830 | 30.99 | 0.1338 | 2.87731 | 0.36 |
| 31.5576 | 35.35 | 0.2007 | 2.83512 | 0.41 |
| 31.9960 | 61.97 | 0.1338 | 2.79726 | 0.72 |
| 34.5173 | 50.78 | 0.2676 | 2.59850 | 0.59 |
| 35.7922 | 61.68 | 0.2676 | 2.50881 | 0.71 |
| 38.2843 | 42.21 | 0.4015 | 2.35104 | 0.49 |
| 39.3257 | 82.72 | 0.1338 | 2.29115 | 0.96 |

Figure 29:
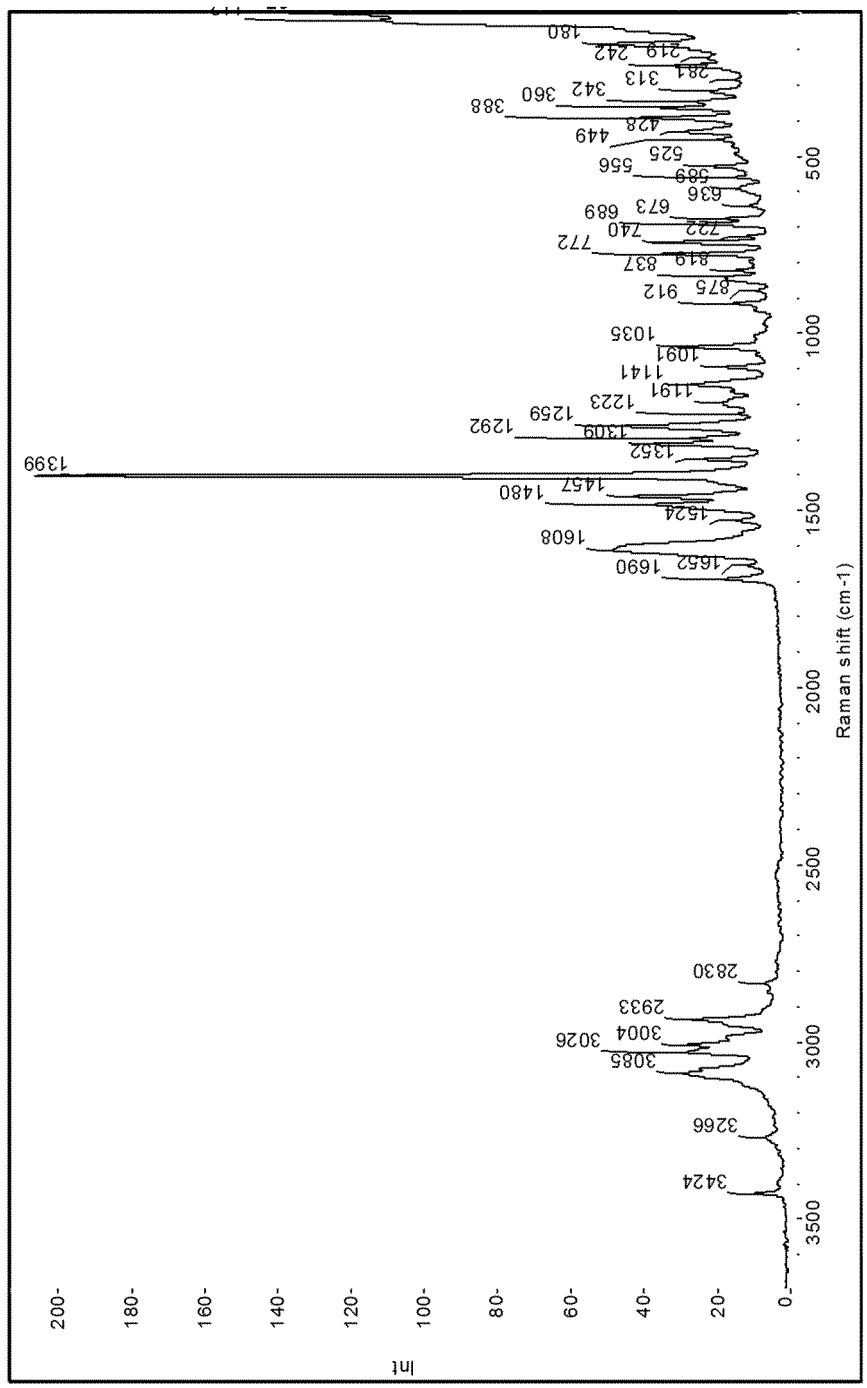
FIG. 29: FT-Raman spectrum of Lenvatinib, form FOA-1

FT-Raman analysis returns the spectrum shown in FIG. 29. The spectrum reports the characteristic bands of form FOA-1.

Figure 30:
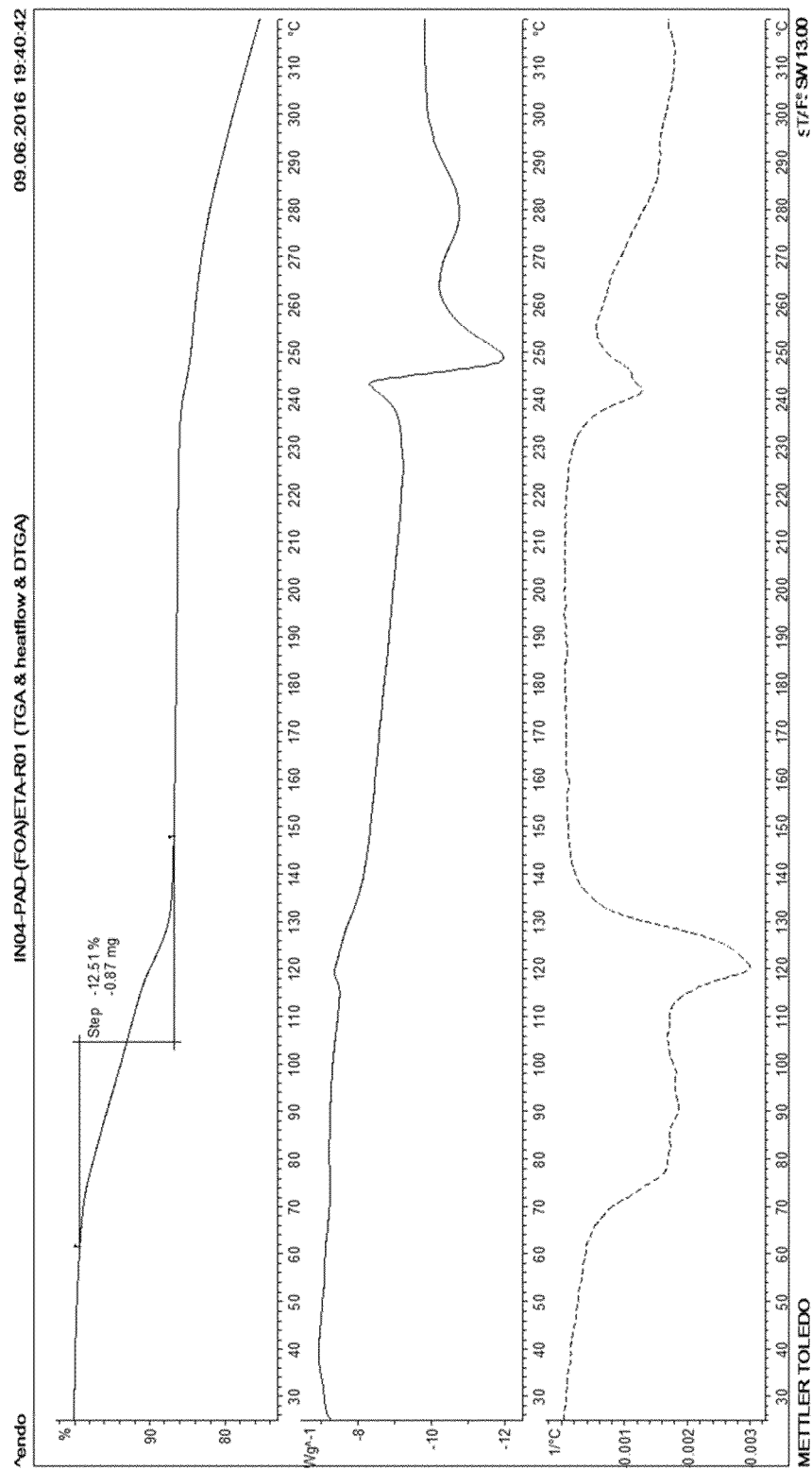
FIG. 30: TGA analysis of Lenvatinib, form FOA-1

The TGA analysis, shown in FIG. 30, highlights a combination of two step weight loss of 12.5% (between approx. 60 and 140° C.) and then the melting/degradation of the sample above 220° C. An endothermic peak in the heat-flow during the loss of weight was present.

Figure 31:
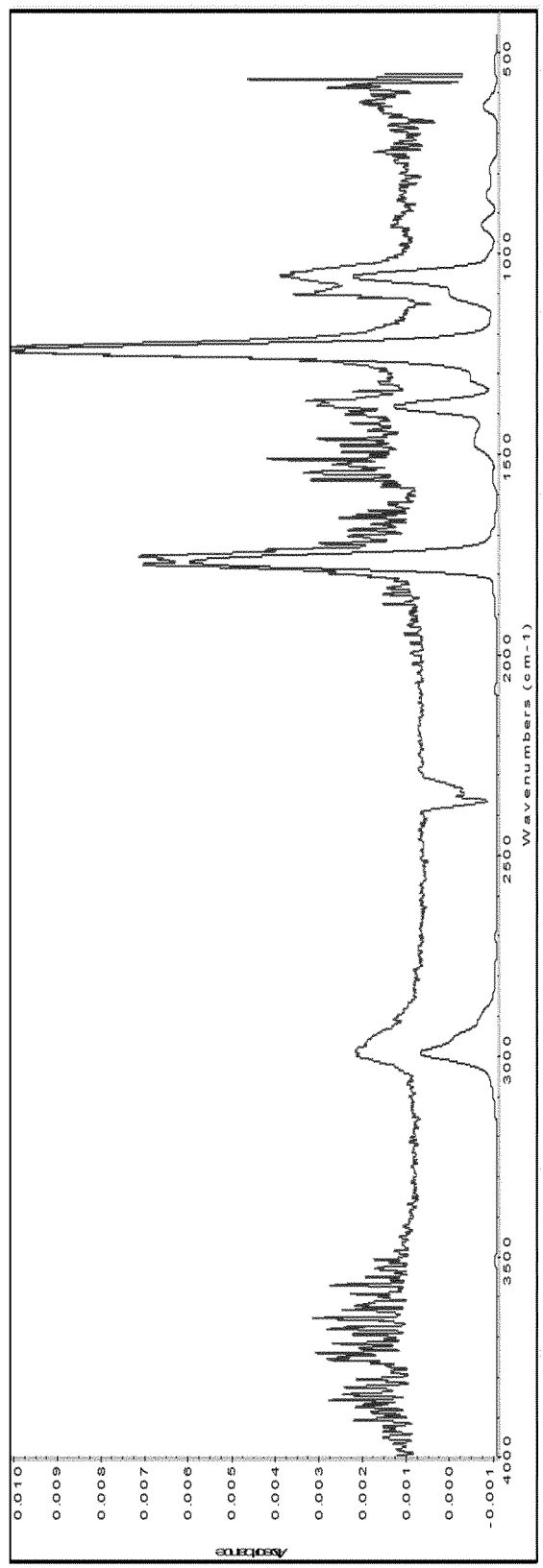
FIG. 31: EGA analysis of Lenvatinib, form FOA-1

The EG analysis shows that the weight loss was due to the loss of formic acid and ethyl acetate (see FIG. 31).

Example 7: H₂O-1

Lenvatinib Mesylate (100-1000 mg) in anhydrous or hydrate form was suspended in water (10-100 mL) and stirred for 1-7 days at a temperature from room temperature to the boiling point of water. The viscous liquid obtained was dried at a temperature from 30 to 80° C. and at a pressure from 1 to $10^{-2}$ atm.

The Lenvatinib mesylate H₂O-1 of the invention is an anhydrous crystal form, characterized by evaporation in different conditions of the very viscous liquid obtained stirring for several hours the crystal Form A in pure water. This viscous liquid (similar to a gel) was also obtained by kneading and by heating/cooling cycles of the suspension of Form A in pure water.

The preferred evaporation conditions tested were:
60° C./approx. 1 atm
40° C./$10^{-2}$ atm
30° C./$10^{-2}$ atm.

The solid was recovered in a yield ~99% and high level of chemical purity (>99.5%).

Figure 32:
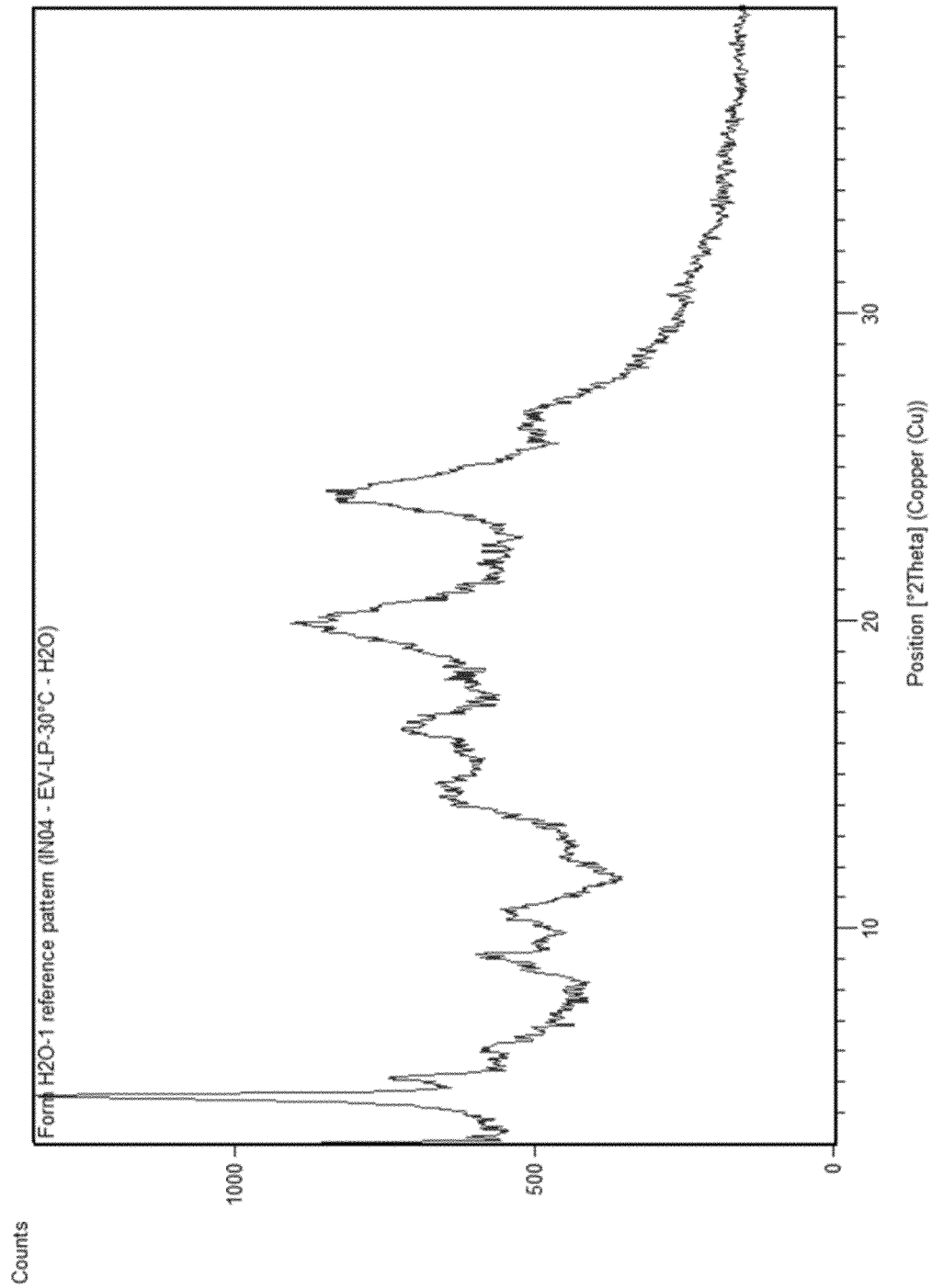
FIG. 32: XRPD spectrum of Lenvatinib, form $H_2O$-1

The new crystal form H₂O-1 is characterized by the XRPD spectrum shown in FIG. 32. Main peaks at 2theta±0.3 degrees are: 4.5, 5.1, 9.1, 10.5, 19.9, 24.1. Table 7 below shows the significant peaks of the spectrum.

TABLE 7

XRPD peak list

| Pos. [°2Th.] | FWHM [°2Th.] | Area [cts*°2Th.] | Height [cts] | Rel. Int. [%] |
|---|---|---|---|---|
| 4.516 | 0.2895 | 184.8 | 504.5 | 100 |
| 5.1194 | 0.2691 | 44.1 | 140.81 | 27.91 |
| 6.0497 | 0.3396 | 18.39 | 43.5 | 8.62 |
| 9.0617 | 0.7832 | 94.94 | 96.36 | 19.1 |
| 10.4869 | 0.6148 | 83.66 | 113.89 | 22.58 |
| 14.079 | 0.7454 | 95.37 | 99.99 | 19.82 |
| 16.5072 | 0.5667 | 108.54 | 99.76 | 19.77 |

TABLE 7-continued

XRPD peak list

| Pos. [°2Th.] | FWHM [°2Th.] | Area [cts*°2Th.] | Height [cts] | Rel. Int. [%] |
|---|---|---|---|---|
| 19.8636 | 0.7933 | 272.15 | 178.67 | 35.42 |
| 24.0138 | 0.68 | 285.02 | 218.3 | 43.27 |
| 26.8983 | 0.7933 | 102.01 | 66.97 | 13.28 |

Figure 33:
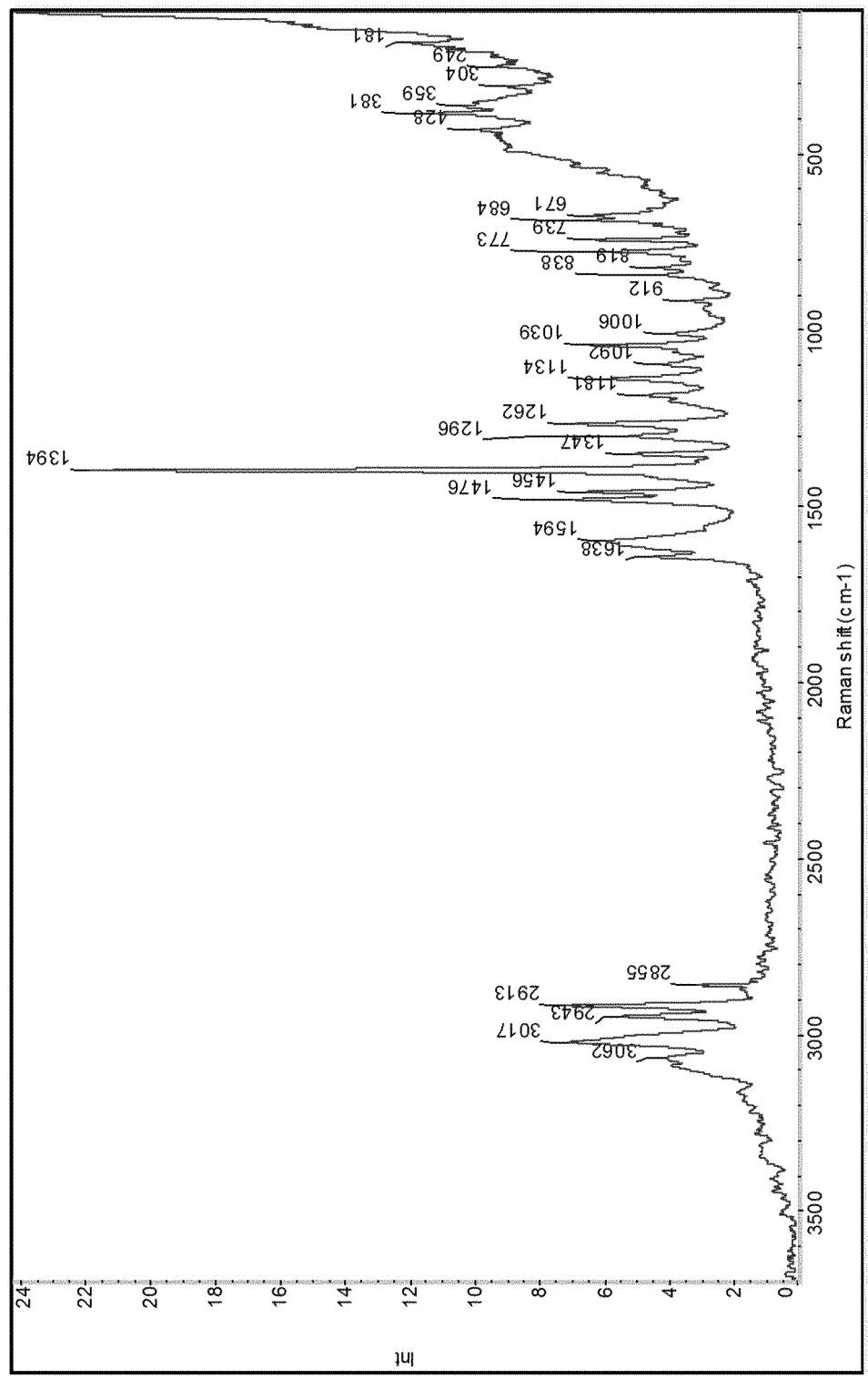
FIG. 33: FT-Raman spectrum of Lenvatinib, form $H_2O$-1

FT-Raman analysis returns the spectrum shown in FIG. 33. The spectrum reports the characteristic bands of form H₂O-1.

Figure 34:
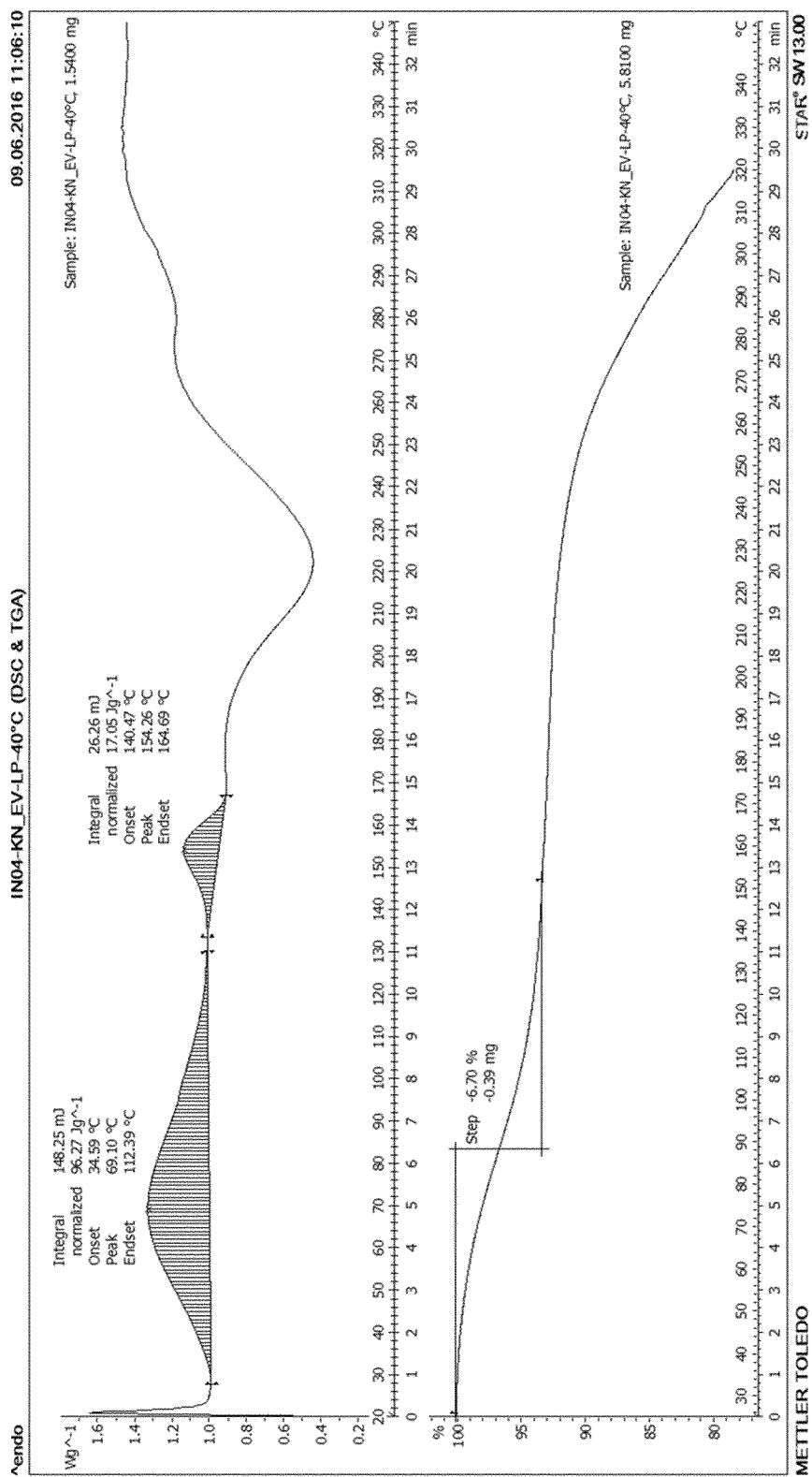
FIG. 34: DSC analysis of Lenvatinib, form $H_2O$-1

DSC analysis, shown in FIG. 34, highlights two endothermic events: the first peak at approx. 69° C. (onset=34.6° C.) is broad and it was associated to the loss of water; the second peak at 154° C. (onset=140.5° C.) can be associated to the melting of the sample.

Figure 35:
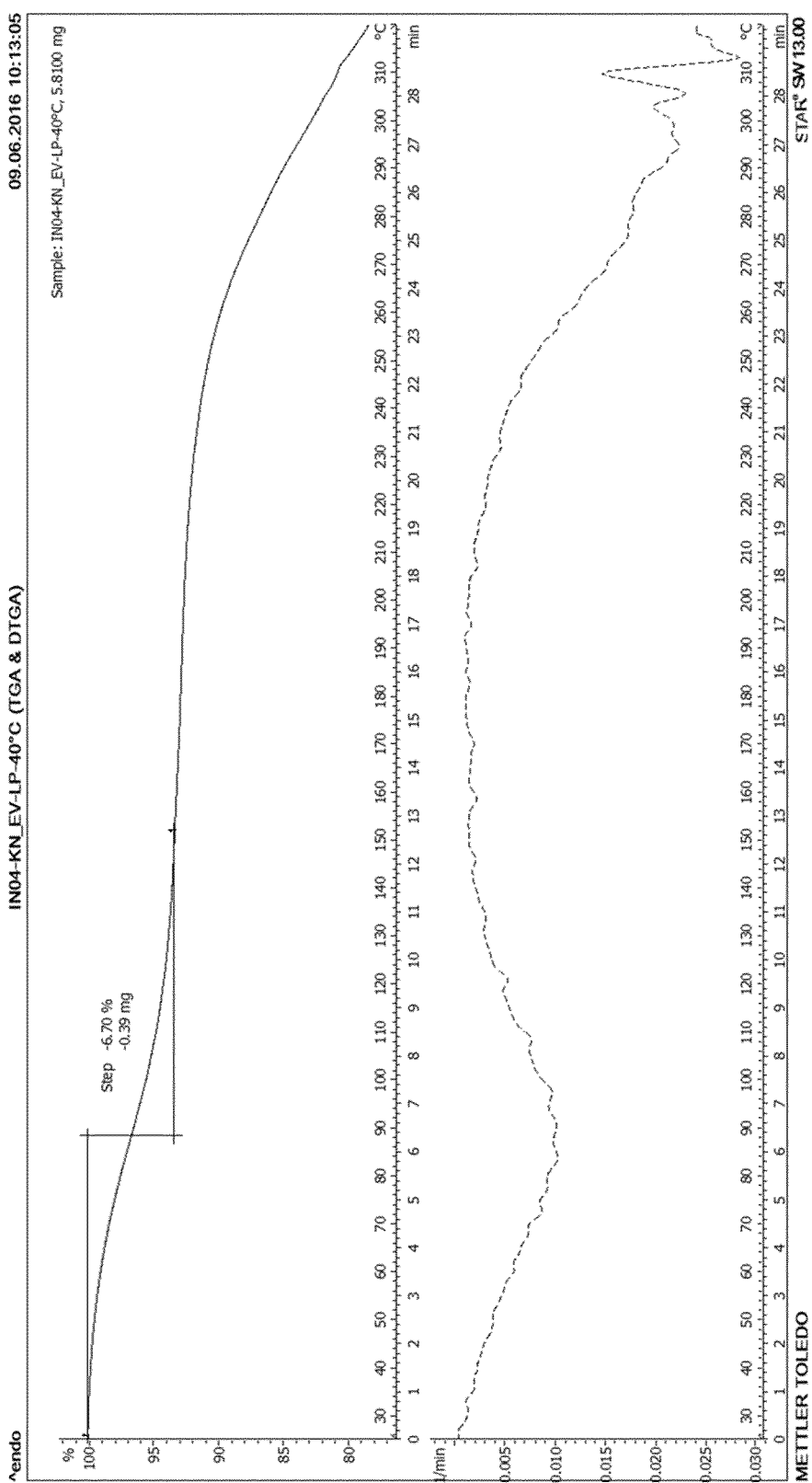
FIG. 35: TGA analysis of Lenvatinib, form $H_2O$-1
Figure 36:
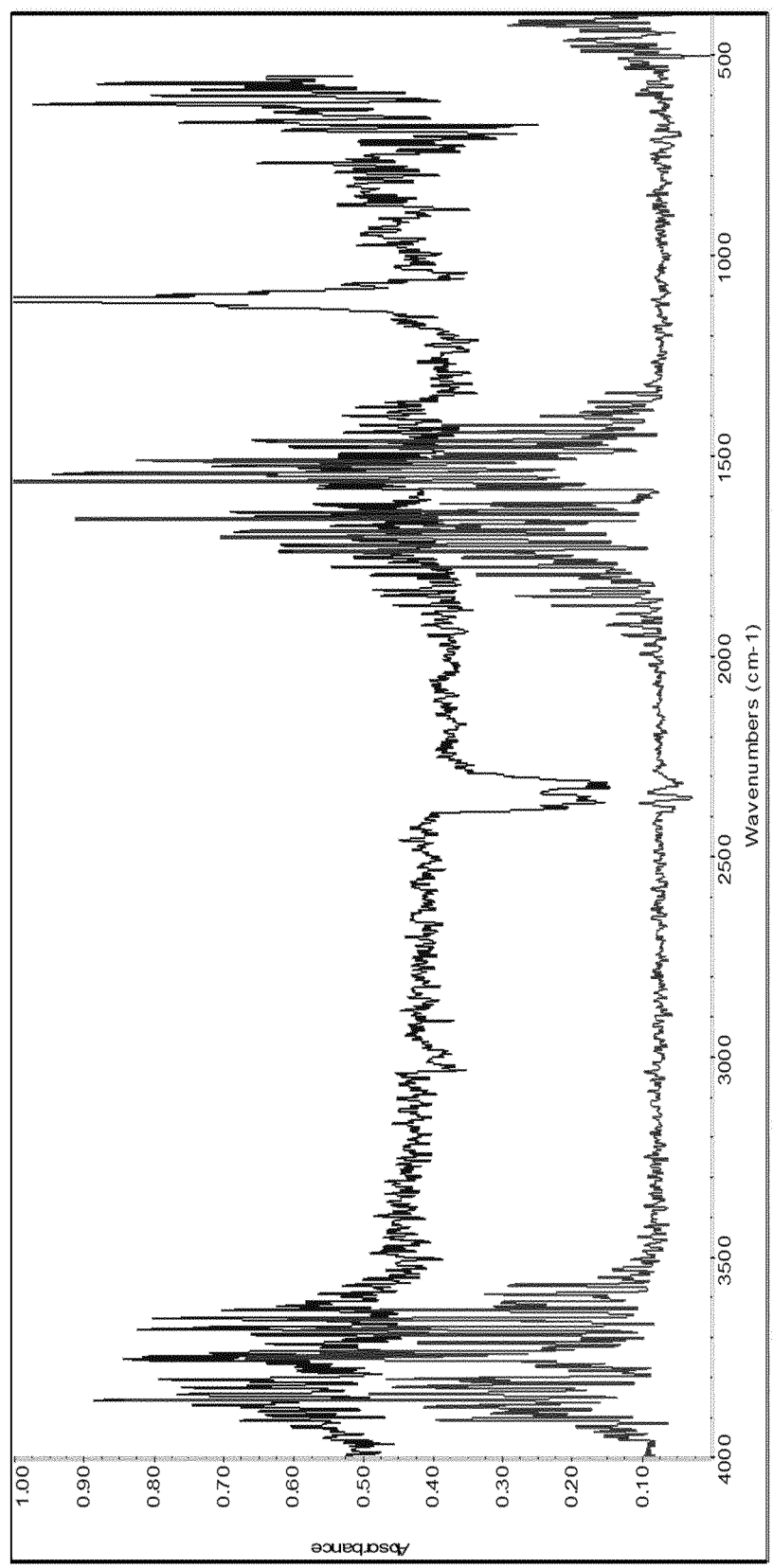
FIG. 36: EGA analysis of Lenvatinib, form $H_2O$-1
Figure 37:
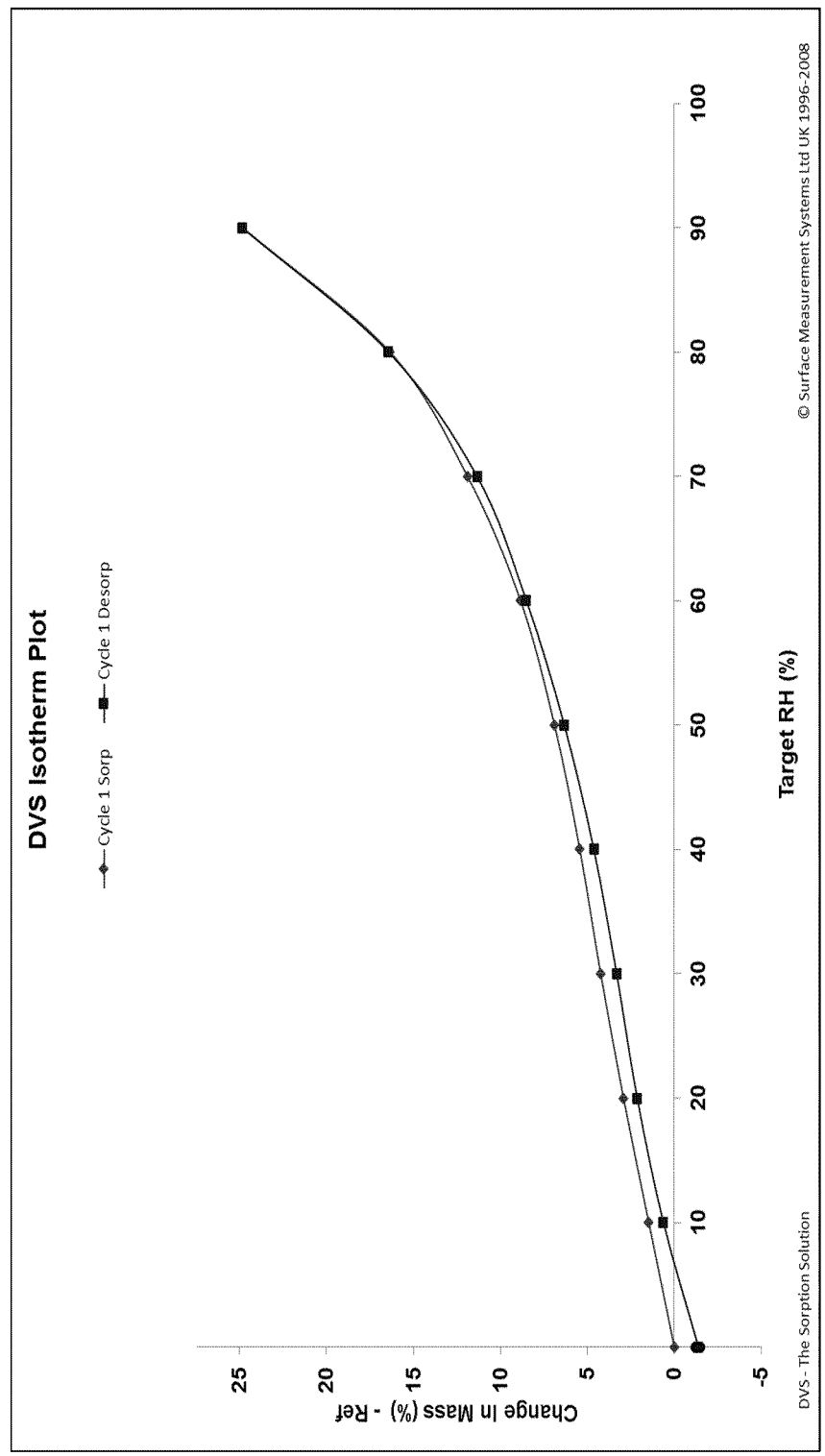
FIG. 37: DVS analysis of Lenvatinib, form $H_2O$-1

The TGA analysis, shown in FIG. 35, highlights a broad weight loss of 6.7%, between approx. 25 and 150° C., associated to the evaporation of water (as confirmed by EG analysis), and then the degradation of the sample after 200° C. (confirmed by EGA analysis FIG. 36).

In DVS analysis, shown in FIG. 22, the sorption and desorption of water was reversible and the analysis did not evidence any event.

The sample recovered at the end of DVS analysis was analyzed by XRPD: its diffractogram did not show any important modification.

The data recorded by DVS analysis showed a mass increased percentage of 10.9% between 40% end 80% RH of the absorption cycle: the sample was classified as hygroscopic.

The invention claimed is:
1. A polymorph of Lenvatinib mesylate which is
   a crystal form, designated as form ACA-1 HT DRY, characterized by an XRPD spectrum (Kα1) showing the main peaks at 2theta ±0.3 degrees 6.0, 7.7, 11.2, 13.6, 19.4, 20.0, 23.1, 26.9.

* * * * *